(12) United States Patent
Kim et al.

(10) Patent No.: US 12,127,870 B2
(45) Date of Patent: Oct. 29, 2024

(54) MOBILE MEDICAL IMAGE APPARATUS FOR PROVIDING DIGITAL TOMOSYNTHESIS AND OPERATION METHOD THEREOF

(71) Applicant: JPI Healthcare CO., LTD., Seoul (KR)

(72) Inventors: Kyong-Woo Kim, Jeollabuk-do (KR); Eun-Kyu Park, Seoul (KR); Jin-Guk Kim, Seoul (KR)

(73) Assignee: JPI Healthcare CO., LTD., Seoul (KR)

( * ) Notice: Subject to any disclaimer, the term of this patent is extended or adjusted under 35 U.S.C. 154(b) by 281 days.

(21) Appl. No.: 17/704,242

(22) Filed: Mar. 25, 2022

(65) Prior Publication Data

US 2023/0277146 A1 Sep. 7, 2023

(30) Foreign Application Priority Data

Mar. 4, 2022 (KR) .......................... 10-2022-0028047

(51) Int. Cl.
| | |
|---|---|
| *A61B 6/40* | (2024.01) |
| *A61B 6/00* | (2006.01) |
| *A61B 6/02* | (2006.01) |
| *A61B 6/46* | (2024.01) |
| *A61B 6/50* | (2024.01) |

(52) U.S. Cl.
CPC ............ *A61B 6/4441* (2013.01); *A61B 6/025* (2013.01); *A61B 6/4405* (2013.01); *A61B 6/4447* (2013.01); *A61B 6/466* (2013.01); *A61B 6/502* (2013.01); *A61B 2576/02* (2013.01)

(58) Field of Classification Search
CPC ...... A61B 6/4441; A61B 6/025; A61B 6/4405
See application file for complete search history.

(56) References Cited

U.S. PATENT DOCUMENTS

| | | | |
|---|---|---|---|
| 2013/0077765 A1* | 3/2013 | Welsh ................. | A61B 6/4441 378/197 |
| 2019/0216415 A1* | 7/2019 | Wojcik ............... | A61B 6/4283 |
| 2020/0121267 A1* | 4/2020 | Deutschmann ...... | A61B 6/4452 |
| 2020/0323503 A1* | 10/2020 | Heath ................. | A61B 6/4405 |
| 2023/0218251 A1* | 7/2023 | Hansroul ............. | A61B 6/547 378/4 |

FOREIGN PATENT DOCUMENTS

KR 10-2016-0094565 A 8/2016

* cited by examiner

*Primary Examiner* — Hugh Maupin
(74) *Attorney, Agent, or Firm* — The PL Law Group, PLLC

(57) ABSTRACT

A medical image apparatus according to an embodiment of the present disclosure includes a main body that is travelable, a column vertically coupled to the main body, a straight arm moving unit sliding in a longitudinal direction of the column, a straight arm coupled to the straight arm moving unit and rotating with respect to the column, and a source arm located on a side of the straight arm, perpendicular to the straight arm, and including a source driving rail through which a source assembly slides, wherein the straight arm is coupled to a moving unit rotating shaft formed on the straight arm moving unit, and is rotatable with respect to the column about the moving unit rotating shaft, and the source arm is fixed to the side of the straight arm.

8 Claims, 22 Drawing Sheets

FIG. 13
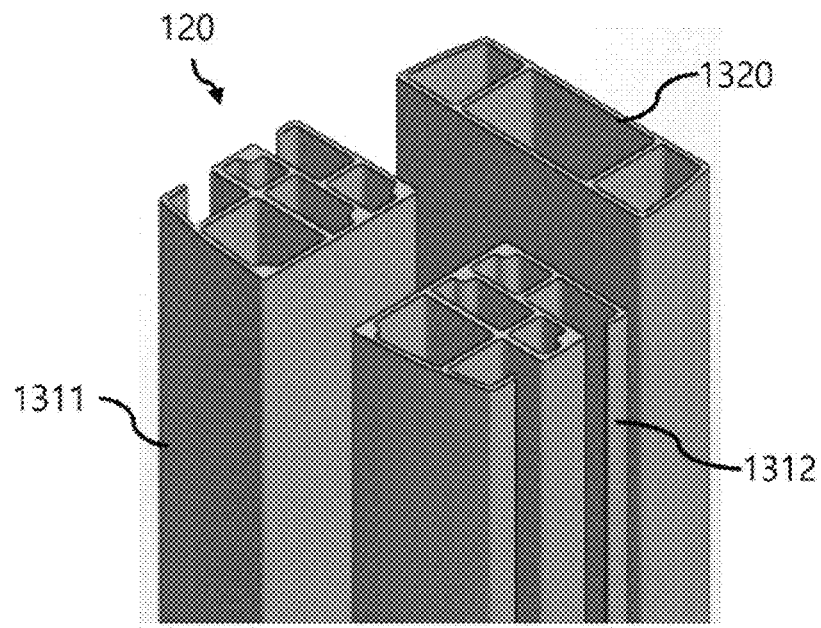
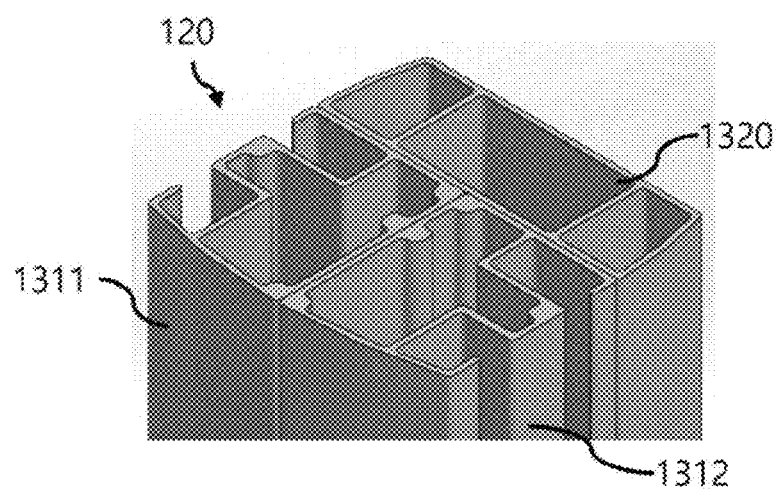

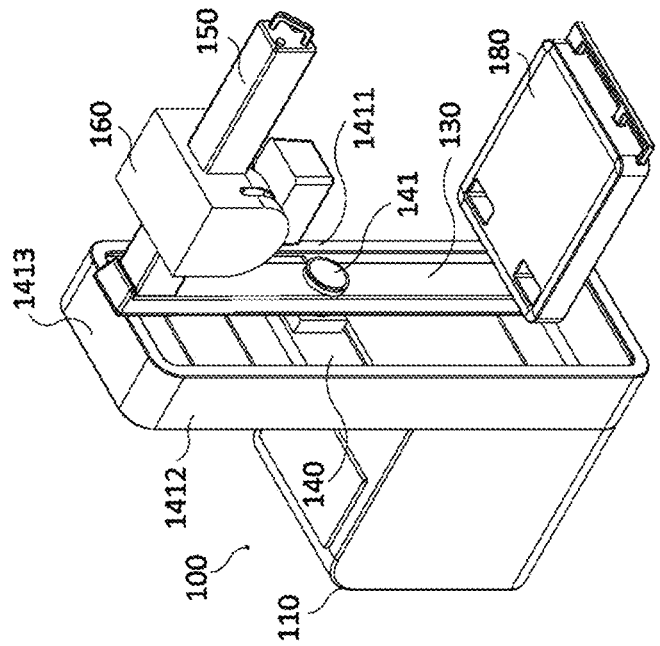
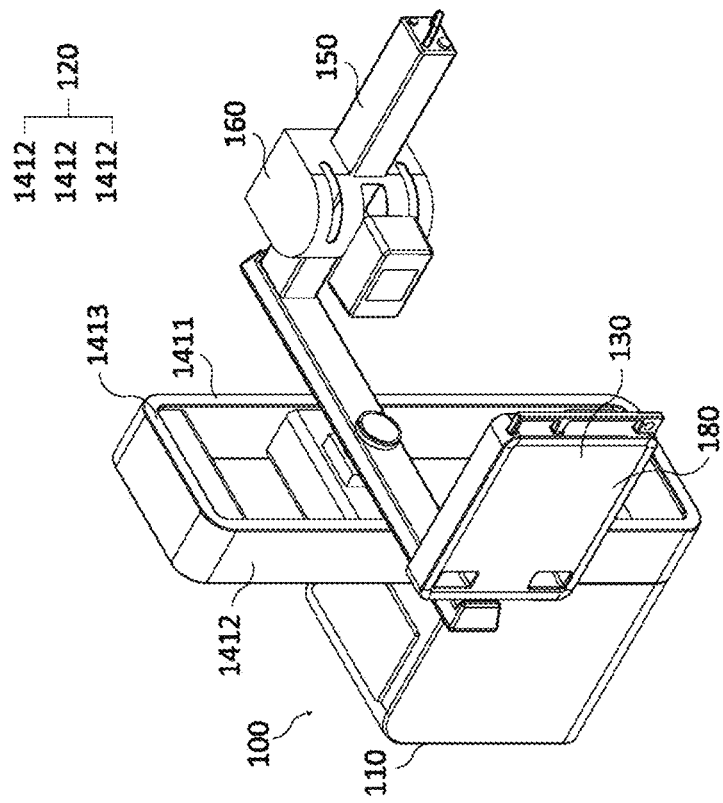
FIG. 14

FIG. 16
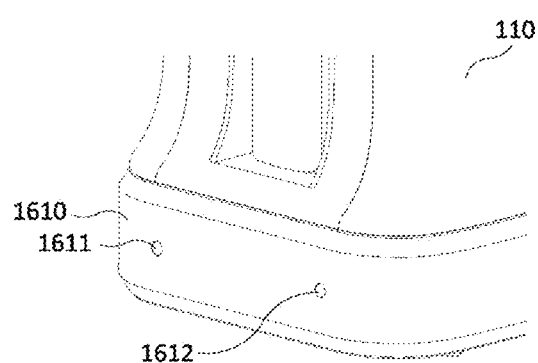
(a)
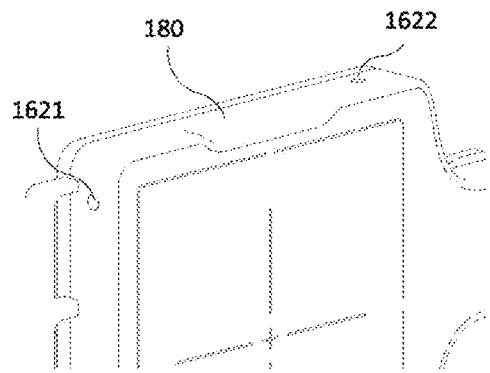
(b)
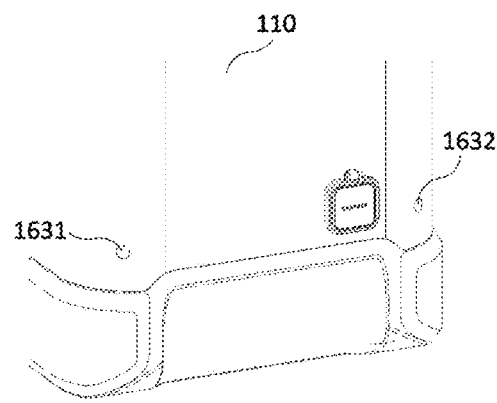
(c)
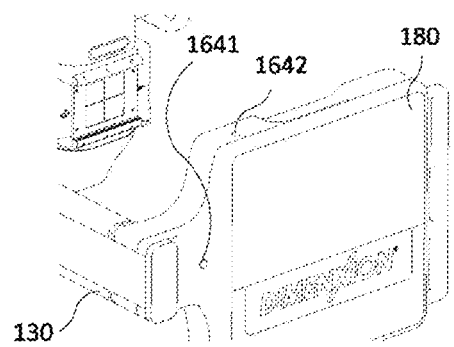
(d)

FIG. 20
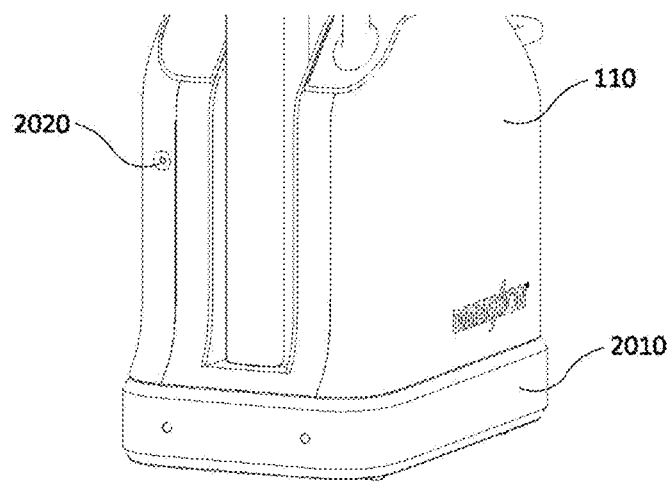
(a)
(b)

MOBILE MEDICAL IMAGE APPARATUS FOR PROVIDING DIGITAL TOMOSYNTHESIS AND OPERATION METHOD THEREOF

CROSS-REFERENCE TO RELATED APPLICATION

This application claims the benefit under 35 USC § 119 of Korean Patent Application No. 10-2022-0028047, filed on Mar. 4, 2022, in the Korean Intellectual Property Office, the entire disclosure of which is incorporated herein by reference for all purposes.

BACKGROUND

1. Technical Field

The present disclosure relates to a mobile medical image apparatus for providing digital tomosynthesis, and more particularly, to a medical image apparatus capable of capturing a two-dimensional (2D) or three-dimensional (3D) image of an object. An operation of the medical image apparatus for providing digital tomosynthesis may be controlled based on various sensors.

2. Description of the Related Art

As radiographic medical imaging apparatuses, imaging apparatuses using X-rays have been developed and used. In an X-ray imaging apparatus, when an X-ray emitted from an X-ray source passes through an object, a scintillator of the X-ray imaging apparatus converts the X-ray, which has passed through the object, into visible light according to the density of the object, and the visible light is converted into an electrical signal via a photodiode provided in the X-ray imaging apparatus. The X-ray imaging apparatus represents a digital image of the object through which the X-ray has passed by using the electrical signal.

In general, a collimator refers to a device for transforming diverging light emitted from a point light source into parallel light. Making parallel light is required for professional measurements in spectroscopy, geometry, and physical optics. In particular, a collimator used in radiology is an absorber that adjusts the size of a beam and the degree of angular spread of beams of X-rays, gamma rays, and nuclear particles according to special purposes. That is, a collimator is generally used as a means for adjusting X-rays or gamma rays so that a beam of a constant size is emitted onto an object.

Recently, while X-ray imaging has been rapidly replaced by digital radiography (DR) using digital sensors with the development of semiconductor and image processing technology, X-ray imaging has also been applied and developed in various ways according to purposes.

SUMMARY

The present disclosure relates to a mobile medical image apparatus, and the medical image apparatus may provide digital tomosynthesis. The mobile medical image apparatus of the present disclosure may be miniaturized and may be freely moved. Also, the mobile medical image apparatus may freely change its posture to suit an object that has difficulty moving. Also, the mobile medical image apparatus may recognize surrounding solid objects, to prevent a dangerous situation due to movement.

However, the technical problems are not limited thereto, and there may be other technical problems.

A medical image apparatus according to the present disclosure includes a column vertically coupled to a main body, a straight arm moving unit sliding in a longitudinal direction of the column, a straight arm coupled to the straight arm moving unit and rotating with respect to the column, and a source arm located on a side of the straight arm, perpendicular to the straight arm, and including a source driving rail through which a source assembly slides, wherein the straight arm is coupled to a moving unit rotating shaft formed on the straight arm moving unit, and is rotatable with respect to the column about the moving unit rotating shaft, and the source arm is fixed to the side of the straight arm.

The medical image apparatus may further include a detector arm located on the other side of the straight arm, and including a detector driving unit sliding in a longitudinal direction of the straight arm and including a detector provided to face the source assembly, wherein the detector arm includes a detector sliding portion parallel to the straight arm, and a detector coupling portion perpendicular to the straight arm and coupled to the detector.

The source arm may pass through a hole formed in the source assembly, and a roller formed in the hole of the source assembly may contact the source driving rail so that the source assembly slides through the source driving rail.

Due to the detector driving unit, the detector arm may be located at a first position where a distance between the detector and the source assembly is a first distance, or may be located at a second position where a distance between the detector and the source assembly is a second distance, wherein the first distance is less than the second distance.

When the medical image apparatus travels, the straight arm may be perpendicular to the ground, and the detector arm may be located at the first position and may be located closer to the ground than the source arm.

The detector sliding portion of the detector arm may be inserted into a guide hole formed in the straight arm, and slides in the longitudinal direction of the straight arm.

The straight arm may include a hole formed in the longitudinal direction in the straight arm and a straight arm balance weight located in the hole, and the straight arm balance weight may move in a direction opposite to a sliding direction of the detector arm.

A plurality of rollers formed on both sides of the straight arm moving unit may be vertically movable along a moving unit rail formed in the column.

A medical image apparatus according to the present disclosure includes a column coupled to a main body and vertically extending, a straight arm moving unit sliding in a longitudinal direction of the column and including a moving unit rotating shaft for rotating a straight arm, and the straight arm coupled to the straight arm moving unit and rotating with respect to the column, wherein the straight arm moving unit includes a camshaft formed along a side surface of the moving unit rotating shaft, having an elliptical cross-section, and fixed to the straight arm moving unit, the straight arm includes a first balance unit and a second balance unit fixed to the straight arm, contacting a side surface of the camshaft, and configured to press the side surface of the camshaft by an elastic body, and the first balance unit is configured to press a side of the camshaft and the second balance unit is configured to press the other side of the camshaft.

The straight arm moving unit of the medical image apparatus may include a base portion coupled to the moving unit rotating shaft and having a surface perpendicular to the moving unit rotating shaft, a convex portion connected to both sides of the base portion and vertically extending to support both sides of a front cover of the column, a concave portion connected to the convex portion and vertically extending to be engaged with an open portion of the column, and a roller connecting portion connected to the concave portion and vertically extending to couple a roller.

A roller rotating shaft coupled to the roller connecting portion of the medical image apparatus according to the present disclosure may extend in a left-right direction or may extend in a front-back direction.

The column of the medical image apparatus according to the present disclosure may include a first space portion extending in the longitudinal direction of the column in the column, a second space portion extending in the longitudinal direction of the column in the column and formed in front of the first space portion, a moving unit rail formed on both sides of the second space portion, and a column cover covering the moving unit rail and vertically extending.

A vibration absorbing portion formed of an elastic material and vertically extending may be provided between the main body and the column of the medical image apparatus of the present disclosure.

The column of the medical image apparatus of the present disclosure may include two frames having a first shape and a frame having a second shape, a source arm and a detector arm may include a frame having a first shape, and the straight arm may include a frame having a second shape The two frames having the first shape included in the column may be located in front of the frame having the second shape included in the column of the medical image apparatus according to the present disclosure.

The column of the image medical apparatus according to the present disclosure may include a first column vertically extending and coupled to a left side of the main body, a second column vertically extending and coupled to a right side of the main body, and a column connecting portion configured to connect an upper portion of the first column to an upper portion of the second column, and a moving unit rail for moving a roller of the straight arm moving unit is formed on a right side of the first column and a left side of the second column.

A medical image apparatus according to the present disclosure includes a main body including a controller for controlling the medical image apparatus and being travelable, a column vertically coupled to the main body, a straight arm being rotatable with respect to the column by a straight arm moving unit, a source arm located on a side of the straight arm, perpendicular to the straight arm, and including a source driving rail through which a source assembly slides, and a detector arm located on the other side of the straight arm and including a detector perpendicular to the straight arm, wherein a forward collision avoidance sensor is included in at least one of the detector and the source arm.

The source assembly of the medical image apparatus according to the present disclosure may include a source encoder for measuring a position of the source assembly on the source arm, and when the source assembly is closest to the main body based on the source encoder, the controller may control the medical image apparatus to be movable.

The straight arm of the medical image apparatus according to the present disclosure may include a rotation encoder for measuring a rotation angle of the straight arm with respect to the column, and the controller may determine whether the straight arm is perpendicular to the ground based on the rotation encoder, and when the straight arm is perpendicular to the ground, may control the medical image apparatus to be movable.

The controller of the medical image apparatus according to the present disclosure may determine an acceleration as a first acceleration when a distance to an obstacle measured by the forward collision avoidance sensor is equal to or less than a third distance and may determine an acceleration as a second acceleration when a distance to an obstacle measured by the forward collision avoidance sensor is equal to or less than a fourth distance, wherein the third distance is greater than the fourth distance and an absolute value of the first acceleration is less than an absolute value of the second acceleration.

At least one of the detector or the main body of the medical image apparatus according to the present disclosure may include a side collision avoidance sensor, and when the straight arm is perpendicular to the ground and the side collision avoidance sensor recognizes a solid object, the controller may control the straight arm not to be rotatable.

The main body of the medical image apparatus according to the present disclosure may include a wheel cover for covering a wheel on both sides, and a travel display portion outside the wheel cover, wherein the travel display portion displays information related to travel of the medical image apparatus.

The controller of the medical image apparatus according to the present disclosure may move downward the wheel cover to contact the ground when the medical image apparatus is in an imaging mode, and may move upward the wheel cover when the medical image apparatus is in a travel mode.

The main body of the medical image apparatus according to the present disclosure may include a camera for capturing a front image of the main body and a main display portion for displaying a medical image, and the controller may control the main display portion to display information related to a medical image when the medical image apparatus is in an imaging mode and may control the main display portion to display an image of the camera when the medical image apparatus is in a travel mode.

A program for performing an operation method of the medical image apparatus may be recorded on a computer-readable recording medium.

Because a medical image apparatus of the present disclosure is movable, the medical image apparatus may freely move to a position where there is a patient. Accordingly, the medical image apparatus may move to a patient who has difficulty moving and may perform X-ray imaging.

Also, the medical image apparatus of the present disclosure may capture a medical image regardless of a posture of a seriously ill patient who has difficulty moving and thus is lying in bed in a place such as an intensive care unit or an emergency room. That is, the medical image apparatus of the present disclosure may provide radiographic imaging while the patient is lying on the bed without moving the patient lying on the bed to a radiation room or the like. The medical image apparatus of the present disclosure may also provide radiographic imaging even in a state where a patient is standing.

Also, the medical image apparatus of the present disclosure may help medical staff to rapidly diagnose an object by providing not only a two-dimensional (2D) image but also a two-and-a-half dimensional (2.5D) or three-dimensional (3D) image.

However, technical effects of the present disclosure are not limited thereto, and other unmentioned technical effects will be apparent to one of ordinary skill in the art from the following description.

BRIEF DESCRIPTION OF THE DRAWINGS

FIG. 13 is a view illustrating a structure of a column according to various embodiments of the present disclosure.

FIG. 14 is a view illustrating a medical image apparatus according to various embodiments of the present disclosure.

FIG. 16 is a view for describing a position of a collision avoidance sensor according to an embodiment of the present disclosure.

FIG. 20 is a view illustrating a main body according to an embodiment of the present disclosure.

DETAILED DESCRIPTION

Figure 1:
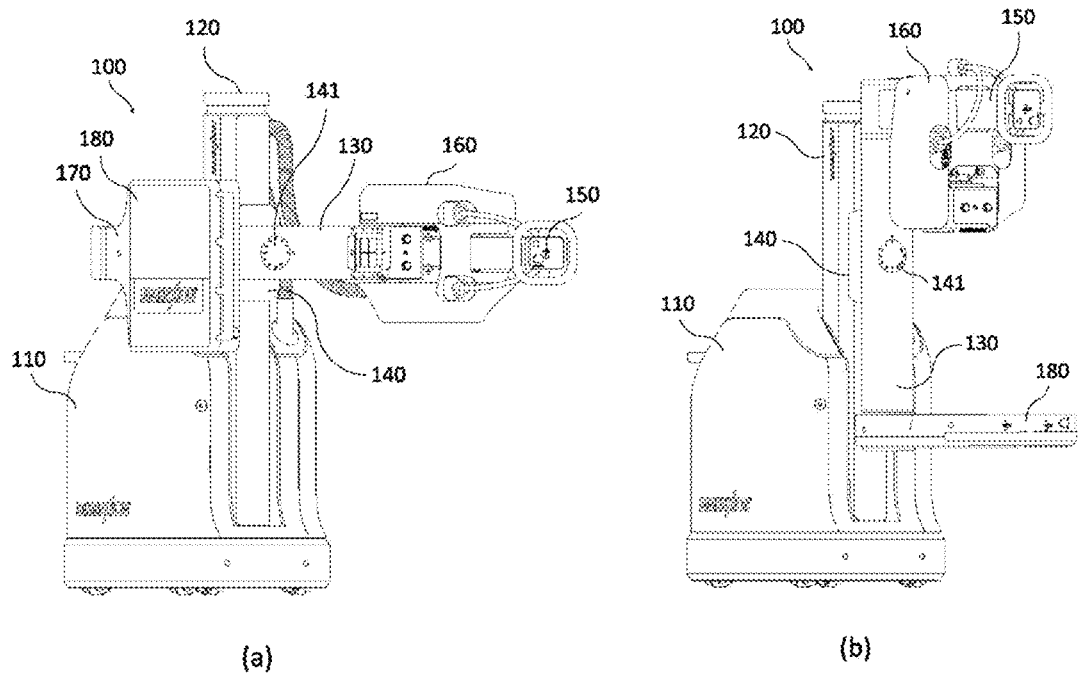
FIG. 1 is a view for describing a medical image apparatus according to an embodiment of the present disclosure.

The advantages and features of the present disclosure and methods of achieving the advantages and features will be described more fully with reference to the accompanying drawings, in which embodiments of the disclosure are shown. The present disclosure may, however, be embodied in many different forms and should not be construed as being limited to the embodiments set forth herein; rather these embodiments are provided so that this disclosure will be thorough and complete, and will fully convey the concept of the present disclosure to one of ordinary skill in the art.

The terms used herein will be briefly described, and disclosed embodiments will be described in detail.

The terms used herein are those general terms currently widely used in the art in consideration of functions in the present disclosure but the terms may vary according to the intention of one of ordinary skill in the art, precedents, or new technology in the art. Also, some of the terms used herein may be arbitrarily chosen by the present applicant, and in this case, these terms are defined in detail below. Accordingly, the specific terms used herein should be defined based on the unique meanings thereof and the whole context of the present disclosure.

As used herein, the singular forms "a," "an," and "the" are intended to include the plural forms as well, unless the context clearly indicates otherwise. Also, the plural forms are intended to include the singular forms as well, unless the context clearly indicates otherwise.

It will be understood that when a certain part "includes" a certain component, the part does not exclude another component but may further include another component, unless the context clearly dictates otherwise.

The term " . . . unit" used herein refers to a software component or a hardware component, which performs certain tasks. However, the term " . . . unit" is not limited to software or hardware. A " . . . unit" may be configured to be in an addressable storage medium or configured to operate one or more processors. Thus, a " . . . unit" may include, by way of example, components such as software components, object-oriented software components, class components, and task components, processes, functions, attributes, procedures, subroutines, segments of program code, drivers, firmware, microcode, circuitry, data, databases, data structures, tables, arrays, and variables. The functionality provided by the components and " . . . units" may be combined into fewer components and " . . . units" or further separated into additional components and " . . . units".

According to an embodiment of the present disclosure, a " . . . unit" may include a processor and a memory. The term "processor" should be interpreted broadly to encompass a general-purpose processor, a central processing unit (CPU), a microprocessor, a digital signal processor (DSP), a controller, a microcontroller, a state machine, and so forth. Under some circumstances, a "processor" may refer to an application specific integrated circuit (ASIC), a programmable logic device (PLD), a field programmable gate array (FPGA), etc. The term "processor" may refer to a combination of processing devices, e.g., a combination of a digital signal processor (DSP) and a microprocessor, a plurality of microprocessors, one or more microprocessors in conjunction with a digital signal processor (DSP) core, or any other such configuration.

The term "memory" should be interpreted broadly to encompass any electronic component capable of storing electronic information. The term "memory" may refer to various types of processor-readable media such as random-access memory (RAM), read-only memory (ROM), non-volatile random-access memory (NVRAM), programmable read-only memory (PROM), erasable programmable read-only memory (EPROM), electrically erasable PROM (EEPROM), flash memory, magnetic or optical data storage, registers, etc. A memory is said to be in electronic communication with a processor when the processor may read information from and/or write information to the memory. A memory integrated in a processor is in electronic communication with the processor.

In the present specification, an actuator refers to an element capable of providing a driving force. Examples of the actuator may include, but are not limited to, a motor, a linear motor, an electronic motor, a direct current (DC) motor, an alternating current (AC) motor, a linear actuator, and an electric actuator.

In the present disclosure, a downward direction may refer to a direction from a medical image apparatus 100 toward the ground, an upward direction may refer to a direction from the ground toward the medical image apparatus 100, and a rearward direction may refer to a direction from a straight arm 130 toward a column 120 or from the column 120 toward a main body 110.

Hereinafter, embodiments of the present disclosure will be described in detail with reference to the attached drawings in order to enable one of ordinary skill in the art to embody and practice the present disclosure. In addition, portions irrelevant to the descriptions of the present disclosure will be omitted in the drawings for clear descriptions of the present disclosure.

FIG. 1 is a view for describing a medical image apparatus according to an embodiment of the present disclosure.

The medical image apparatus 100 may provide mobile digital tomosynthesis. The medical image apparatus 100 may capture a medical image. The medical image may include a two-dimensional (2D), two-and-a-half dimensional (2.5D), or three-dimensional (3D) X-ray image or a computed tomography (CT) image.

The medical image apparatus 100 may include the main body 110. The main body 110 may travel. The main body 110 may include a plurality of wheels, and may include a wheel actuator for providing a driving force to the wheels. The plurality of wheels may be Mecanum wheels. Accordingly, the medical image apparatus 100 may move in a front-back direction and in a left-right direction, and may rotate about an axis perpendicular to the ground. However, the present disclosure is not limited thereto, and the plurality of wheels may be general wheels. The plurality of wheels may receive a signal related to movement from a user through an input unit. The medical image apparatus 100 may drive the wheel actuator based on the signal related to movement. However, the present disclosure is not limited thereto. The medical image apparatus 100 may not include the main body 110 that may travel.

The medical image apparatus 100 may include the column 120. The column 120 may be coupled to the main body 110 of the medical image apparatus. The column 120 may be formed in front of the main body 110 to vertically extend. A vertical direction may refer to a direction perpendicular to the ground. The column 120 may vertically extend and may be coupled to the main body 110. A guide groove (not shown) that vertically extends may be formed in a front surface of the column 120. The guide groove in FIG. 1 is covered by a front cover of the column. The guide groove may guide vertical movement of a straight arm moving unit 140. The column 120 may be fixed to a wall surface or the ground, without being coupled to the main body. The medical image apparatus 100 may be fixed in a medical imaging room.

The medical image apparatus 100 may include the straight arm moving unit 140. The straight arm moving unit 140 may slide in a longitudinal direction of the column 120. The longitudinal direction of the column 120 may be a vertical direction. That is, the straight arm moving unit 140 may move along the guide groove of the column 120.

The medical image apparatus 100 may include the straight arm 130. The straight arm 130 may be coupled to the straight arm moving unit 140 and may move with respect to the column 120. The straight arm moving unit 140 may be coupled to the center of the straight arm 130. The straight arm moving unit 140 may be coupled to the center of the straight arm 130 so that the center of weights of a detector arm 170 and a source arm 150 is located at the straight arm moving unit 140. However, the present disclosure is not limited thereto. The straight arm moving unit 140 may be coupled to the center of weights of the straight arm 130, the detector arm 170, and the source arm 150. Alternatively, the straight arm moving unit 140 may be coupled to an end of the straight arm 130, and the source arm 150 may be coupled to the other end of the straight arm 130.

The straight arm moving unit 140 may be coupled to the straight arm 130. The straight arm 130 may vertically move along the column 120 due to the straight arm moving unit 140. The straight arm 130 may slid along the guide groove of the column 120 due to the straight arm moving unit 140.

The column 120 may function as a support that may stably support the straight arm 130. Also, the column 120 may be formed to have a cross-section having rigidity greater than that of the straight arm 130. A straight arm driving unit capable of causing the straight arm moving unit 140 to may be provided in the column 120. The straight arm driving unit may include at least one of an actuator, a gear, a weight, a pulley, or a pulley cord.

Also, the straight arm 130 may be rotatably coupled to the straight arm moving unit 140. The straight arm 130 may be coupled to a moving unit rotating shaft 141 formed on the straight arm moving unit 140, and may rotate with respect to the column 120 about the moving unit rotating shaft 141. The moving unit rotating shaft 141 may be a shaft extending in a front-back direction. The straight arm 130 may vertically move with respect to the column 120, and may rotate with respect to the column 120. (a) of FIG. 1 may indicate a state where the straight arm 130 is parallel to the ground. When the straight arm 130 rotates by 90°, as shown in (b) of FIG. 1, the straight arm 130 may be perpendicular to the ground.

The medical image apparatus 100 may include the source arm 150. The source arm 150 may be located on a side of the straight arm 130. For example, as shown in (a) of FIG. 1, the source arm 150 may be located on a left side of the straight arm 130. Also, as shown in (b) of FIG. 1, the source arm 150 may be located on an upper side of the straight arm 130. A rear side of the source arm 150 may be coupled to the straight arm 130. The source arm 150 may be immovably fixed to a side of the straight arm 130. The source arm 150 may be perpendicular to the straight arm 130. Also, the source arm 150 may include a source driving rail through which a source assembly 160 slides. The source driving rail may be provided in the source arm 150 but the present disclosure is not limited thereto. The source driving rail may be provided outside the source arm 150. The straight arm 130 of the medical image apparatus 100 may be coupled to the source arm 150 but may not be coupled to the detector arm 170. The straight arm 130 not including the detector arm 170 will be described with reference to FIG. 2.

The medical image apparatus 100 may include the detector arm 170. The detector arm 170 may be located on the other side of the straight arm 130. The detector arm 170 may be provided to face the source arm 150. For example, as shown in (a) of FIG. 1, the detector arm 170 may be located on a right side of the straight arm 130. Also, for example, as shown in (b) of FIG. 1, the source arm 150 may be located on a lower side of the straight arm 130. The detector arm 170 may slide in a longitudinal direction of the straight arm 130. For example, when the straight arm 130 is located as shown in (a) of FIG. 1, the detector arm may slide in a left-right direction. Also, when the straight arm 130 is located as shown in (b) of FIG. 1, the detector arm may slide in an up-down direction. The medical image apparatus 100 may include a detector driving unit. The detector driving unit may be an element for sliding the detector arm 170 along the straight arm 130. The detector driving unit may be included in at least one of the detector arm 170 or the straight arm 130. The detector driving unit may include at least one of an actuator, a gear, a weight, a pulley, or a cord. The detector arm 170 may include a detector 180. The detector 180 may be provided to face the source assembly 160.

As such, in the medical image apparatus 100, the source arm 150, the straight arm 130, and the detector arm 170 may form a "C" shape. The difference from a "C" shape of an existing medical image apparatus is that the source assembly may move independently of the source arm 150 and the detector arm may move with respect to the straight arm. As such, because a degree of freedom of movement is higher than that in the existing medical image apparatus, various types of medical images may be captured. Also, regardless of whether a patient is able to move, the medical image apparatus 100 may obtain a medical image of the patient as arms of the medical image apparatus 100 move. Medical staff may make an accurate diagnosis based on various types of medical images captured by the medical image apparatus 100.

The straight arm 130 of the medical image apparatus 100 may be coupled to the source arm 150 but may not be coupled to the detector arm 170. The straight arm 130 not including the detector arm 170 will be described with reference to FIG. 2.

Figure 2:
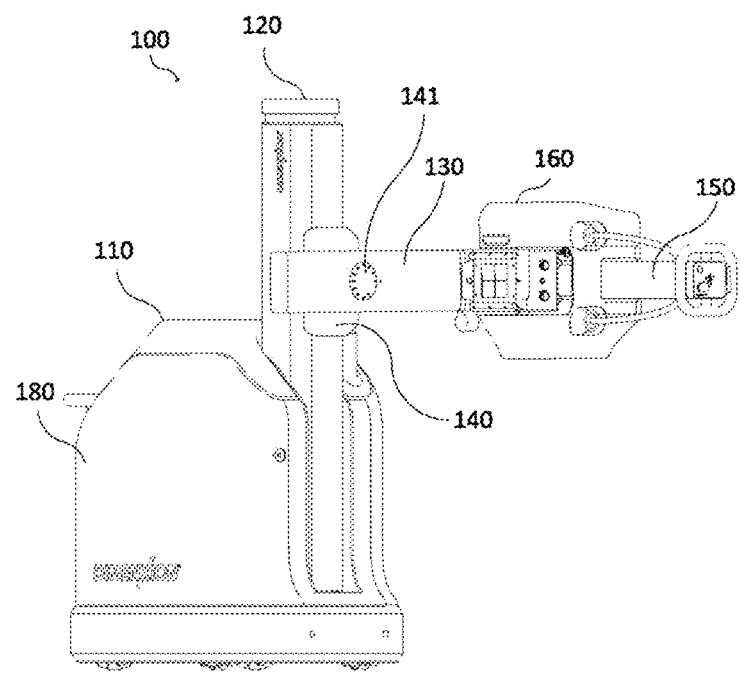
FIG. 2 is a view for describing a medical image apparatus according to an embodiment of the present disclosure.

FIG. 2 is a view for describing a medical image apparatus according to an embodiment of the present disclosure.

FIG. 2 may include some elements that are the same as those in FIG. 1. When compared to FIG. 1, new elements of FIG. 2 will be mainly described. Elements not described in FIG. 2 may be understood with reference to the description of FIG. 1.

The medical image apparatus 100 may include the straight arm 130. The source arm 150 may be located on a side of the straight arm 130. The other side of the straight arm 130 may be coupled to the straight arm moving unit 140. The straight arm 130 may not be coupled to the detector arm 170 or the detector 180. The detector 180 may be accommodated in a detector receiving unit provided on a side surface of the main body 110. During X-ray imaging, a user may take the detector 180 out of the main body 110 and may capture an image of an object by using the source assembly 160 of the medical image apparatus 100 with the detector 180 on a rear surface of an object. After imaging, the detector 180 may be accommodated again in the detector receiving unit of the main body 110. The detector 180 may be charged in the detector receiving unit.

When the medical image apparatus 100 is a mobile apparatus, positions of the detector 180 and the source assembly 160 may be freely adjusted independently. In this case, as a positional relationship between the detector 180 and the source assembly 160 continuously changes, the positional relationship between the detector 180 and the source assembly 160 may change whenever imaging is performed. Also, the positional relationship between the detector 180 and the source assembly 160 may continuously change even during imaging. Accordingly, the quality of a medical image captured by the medical image apparatus 100 may not be uniform and may not be clear.

In order to solve the problem, the medical image apparatus 100 may further include a light guiding unit and a position tracking unit including a position sensor in addition to the source assembly 160 and the detector 180.

The light guiding unit may be provided on the source assembly 160 or the source arm 150, and may generate guide light for guiding an imaging reference position and may emit the guide light to the detector 180. The position tracking unit includes at least one position sensor attached to the detector 180. In this case, examples of the position sensor may include, but are not limited to, a gyro sensor and an acceleration sensor.

The user may locate the detector 180 at an imaging reference position by referring to the guide light from the source assembly 160 or the source arm 150 and then may input a position tracking start to the medical image apparatus 100. The medical image apparatus 100 may set and store a position of the detector 180 at a position tracking start point as an imaging reference position. Also, the position sensor may accumulate and measure a position change value per unit time based on the imaging reference position. The medical image apparatus 100 tracks a relative position value of the detector with respect to the imaging reference position based on the position change value per unit time that is accumulated and measured.

The medical image apparatus 100 may position-correct each medical image for each imaging angle, obtained by the detector 180 based on the relative position value of the detector with respect to the imaging reference position. Accordingly, the medical image apparatus 100 may generate a medical image without shaking. The medical image for each imaging angle may refer to a medical image captured while the source assembly 160 moves along the source arm 150. When the source assembly 160 moves along the source arm 150, an angle between a line segment from the center of the source assembly 160 to the center of the detector 180 and a surface of the object may change. That is, the medical image apparatus 100 may capture an image of the object at various angles.

The light guiding unit may emit guide light at a point of the source assembly 160, and the guide light may have a quadrangular pyramid shape. The light guiding unit may be located at an apex of a quadrangular pyramid. The guide light may form a quadrangular shape on the detector 180. The quadrangular shape formed on the detector 180 may be referred to as an indicator line. However, the present disclosure is not limited thereto, and the light guiding unit may emit guide light at a point of the source assembly 160, and the guide light may have a triangular shape. The guide light may form a line segment on the detector 180. The light guiding unit may form a plurality of line segments on the detector by emitting a plurality of triangular shapes to the detector 180. Two line segments may form a cross. The line segment formed on the detector 180 may be referred to as an indicator line.

The user may align an outer line of the detector 180 with an indicator line according to guide light, by adjusting a position and a height of a bed on which the detector 180 is placed. When an outer line of the detector 180 is aligned with an indicator line according to guide light, the medical image apparatus 100 may obtain and store a position of the detector 180 as an imaging reference position.

The medical image apparatus 100 may set a position tracking start point (X, Y), and then may accumulate and measure a position change value per unit time of the detector sensed by a position sensor based on the position tracking start point (X, Y). The medical image apparatus 100 may track and monitor a relative position value of the detector with respect to the imaging reference position.

The medical image apparatus 100 may obtain a medical image for each imaging angle, and may obtain a relative position value of the detector with respect to the imaging reference position at a time of capturing the medical image. The medical image apparatus 100 may store the relative position value of the detector corresponding to the obtained medical image. After medical imaging is completed, the medical image apparatus 100 may calculate a position correction value so that the relative position value of the detector is a preset reference position value. Also, the medical image apparatus 100 may correct each medical image for each imaging angle based on the position correction value.

In more detail, in general, the detector 180 may obtain an original medical image including a certain image margin in addition to an image extraction area. The medical image apparatus 100 may adjust a position of the image extraction area according to the position correction value, by considering that the image margin is included in the original medical image. The medical image apparatus 100 may obtain a medical image of the image extraction area in the original medical image. Accordingly, the medical image apparatus 100 may have an effect as if a medical image is obtained while the detector 180 does not move. Even when a positional relationship between the source assembly 160 and the detector 180 frequently changes, all medical images obtained by the medical image apparatus 100 may have position values at the imaging reference position.

When the relative position value of the detector with respect to the imaging reference position increases above a preset value (exceeds the image margin), effective image extraction may not be normally performed. Accordingly, the medical image apparatus 100 of the present disclosure may pre-define a movement limit of the detector by considering the image margin of the medical image, and may generate and output an alarm for requesting realignment of the detector whenever the detector moves beyond the movement limit.

Also, when guide light for guiding the imaging reference position is re-generated along with the alarm, an operator may more easily and accurately realign the detector by referring to the guide light. The medical image apparatus 100 having a position sensor-based position correction function may track and monitor a positional relationship between the source assembly 160 and the detector 180 by using at least one position sensor attached to the detector, and may perform a position-correction operation by reflecting the positional relationship, thereby stably obtaining a clear medical image even when the positional relationship between the source assembly 160 and the detector frequently changes.

Figure 3:
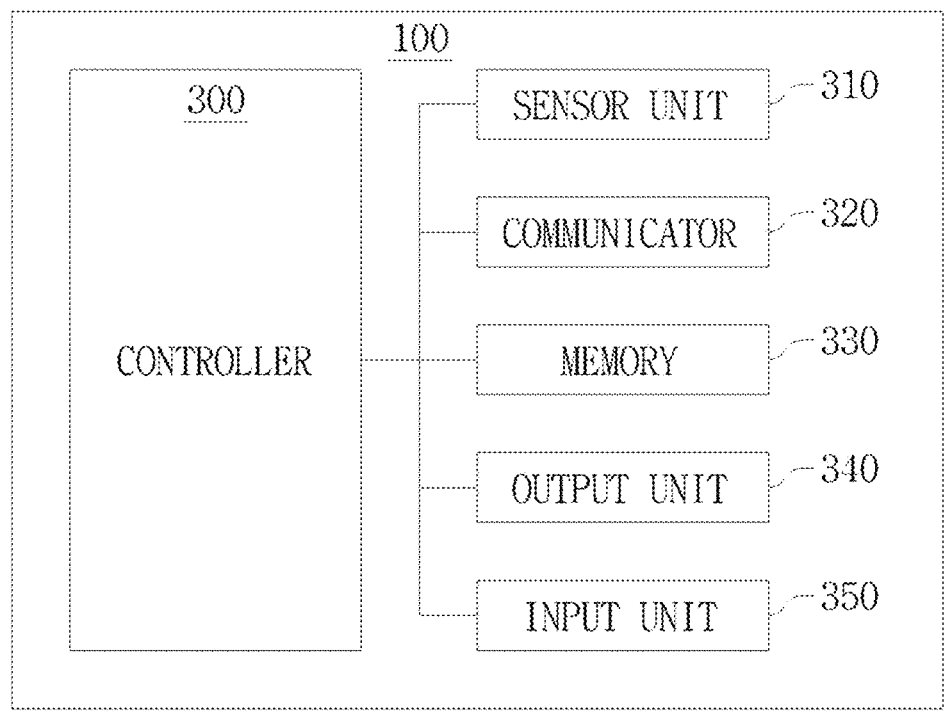
FIG. 3 is a block diagram illustrating various elements that may be included in a medical image apparatus according to an embodiment of the present disclosure.

FIG. 3 is a block diagram illustrating various elements that may be included in a medical image apparatus according to an embodiment of the present disclosure.

The medical image apparatus 100 may include a source assembly, a high voltage generator, a detector, a sensor unit 310, a communicator 320, a memory 330, an output unit 340, an input unit 350, and a controller 300.

The high voltage generator generates a high voltage for generating an X-ray and applies the high voltage to an X-ray source included in the source assembly.

The source assembly may include the X-ray source that receives the high voltage generated by the high voltage generator and generates an X-ray. The X-ray source may include an X-ray tube, and the X-ray tube may be a two-electrode vacuum tube including an anode and a cathode. Also, the source assembly may include a collimator for guiding a path of an X-ray emitted by the X-ray source and adjusting an emission area of the X-ray.

The detector detects an X-ray emitted by the source assembly and transmitted through an object. The detector may be a digital detector. The detector may be implemented by using a thin-film transistor (TFT), or may be implemented by using a charge-coupled device (CCD). The detector may be included in the medical image apparatus 100, or may be a separate device connectable to or separable from the medical image apparatus 100.

The medical image apparatus 100 may include the controller 300. The controller 300 may control an operation of the medical image apparatus 100. For example, the medical image apparatus 100 may include the controller 300 for controlling an operation of a wheel actuator capable of traveling the main body 110, the detector arm 170, or the source assembly 160. The controller 300 may include one processor, or may include a plurality of processors. The controller 300 may be included in the main body 110. When the controller 300 includes a plurality of processors, at least some of the plurality of processors may be physically spaced apart from the main body 110. Also, the medical image apparatus 100 is not limited thereto, and may be implemented in various ways.

According to an embodiment of the present disclosure, the controller 300 may control an operation of the medical image apparatus 100. For example, the medical image apparatus 100 may include a plurality of actuators, and the medical image apparatus 100 may control an operation of the medical image apparatus 100 by controlling operations of the plurality of actuators. For example, the controller 300 may control a detector driving unit for moving the detector arm 170, a straight arm driving unit for vertically moving the straight arm 130, and a source assembly driving unit for moving the source assembly 160. Also, the controller 300 may control imaging of the source assembly.

The medical image apparatus 100 may include the sensor unit 310. The sensor unit 310 may obtain various information by using at least one sensor. The sensor unit 310 may include a sensor using a pressure, potential, or optical measurement means. For example, the sensor unit 310 may include at least one of a distance measurement sensor or an encoder. Also, examples of the sensor may include a pressure sensor, an infrared sensor, an LED sensor, and a touch sensor. However, the present disclosure is not limited thereto. The sensor unit may be included in the main body 110, the straight arm 130, the source arm 150, or the detector arm 170.

Also, the medical image apparatus 100 may include the communicator 320. The communicator 320 may be an element through which the medical image apparatus 100 communicate with an internal module or an external device by wire or wirelessly. Examples of the external device may include an external server and a user terminal. The user terminal may include a personal computer (PC), a smartphone, a tablet, or a wearable device. The communicator 320 may include a wired/wireless communication module for network access. Examples of wireless communication technology may include wireless local area network (WLAN) (Wi-Fi), wireless broadband (Wibro), world interoperability for microwave access (Wimax), and high speed downlink packet access (HSDPA). Examples of wired communication technology may include digital subscriber line (XDSL), fibers to the home (FTTH), and power line communication (PLC). Also, a network connection unit may include a short-range communication module, to transmit and receive data to and from any device/terminal located in a short distance. Examples of short-range communication technology may include, but are not limited to, Bluetooth, radio frequency identification (RFID), infrared data association (IrDA), ultra-wideband (UWB), and Zigbee.

The medical image apparatus 100 may include the memory 330. The controller 300 may execute instructions stored in the memory. The memory 330 may be included in the controller 300 or may be located outside the controller 300. The memory 330 may store various information related to the medical image apparatus 100. For example, the memory 330 may include information related to an operation method of the source assembly 160, and may include a captured image and user authentication information, but the present disclosure is not limited thereto.

The memory 330 may be implemented through a non-volatile storage medium that may continuously store arbitrary data. Examples of the memory 330 may include, but are not limited to, not only a disk, an optical disk, and a magneto-optical storage device, but also a storage device based on a flash memory and/or a battery-backup memory. The memory 330 is a main storage device directly accessed by a processor such as a random-access memory (RAM) such as a dynamic random-access memory (DRAMO) or a static random-access memory (SRAMO), and may refer to, but is not limited to, a volatile storage device in which stored information is quickly lost when power is interrupted. The memory 330 may be operated by the controller 300.

Also, the medical image apparatus 100 may further include a manipulation unit for providing an interface for manipulating the medical image apparatus 100. The manipulation unit may include the output unit 340 and the input unit 350.

The output unit 340 may display imaging-related information such as emission of an X tray or may output sound and an image for checking a state of the main body 110, under the control of the controller 200. The output unit 340 may include a speaker or a display. The output unit 240 may output a medical image generated by the controller 200. The output unit 340 may output information required for a user to manipulate the medical image apparatus 100 such as user interface (UI), user information, or object information. Examples of the output unit 340 may include a speaker, a printer, a cathode-ray tube (CRT) display, a liquid-crystal display (LCD), a plasma display panel (PDP) display, an organic light-emitting diode (OLED) display, a field emission display (FED), a light-emitting diode (LED) display, a vacuum fluorescent display (VFD) display, a digital light processing (DLP) display, a flat panel display (FPD) display, a 3D display, and a transparent display, and may include various other output devices within the scope apparent to one of ordinary skill in the art.

The medical image apparatus 100 may be connected to a workstation by wire or wirelessly. The workstation may exist in a space physically separated from the medical image apparatus 100.

The workstation may include a storage server. The storage server may store a medical image, information about an object, and information about a user (medical staff). The workstation may include a review device. The review device may receive a medical image from the storage server based on the user's command and may diagnose the medical image. The workstation and the medical image apparatus 100 may transmit, store, process, and output data according to the digital imaging and communications in medicine (DICOM) standard. Also, the workstation may include a picture archiving and communication system (PACS).

The workstation may include an output unit, an input unit, and a controller. The output unit and the input unit provide the user with an interface for manipulating the workstation and the medical image apparatus 100. The controller of the workstation may control the workstation and the medical image apparatus 100.

The medical image apparatus 100 may be controlled through the workstation, and may also be controlled by the controller 200 included in the medical image apparatus 100. Accordingly, the user may control the medical image apparatus 100 through the workstation, or may control the medical image apparatus 100 through the controller 200 and the manipulation unit included in the medical image apparatus 100. In other words, the user may remotely control the medical image apparatus 100 through the workstation, or may directly control the medical image apparatus 100.

The controller of the workstation and the controller 200 of the medical image apparatus 100 may be separate, but the present disclosure is not limited thereto. The controller of the workstation and the controller 200 of the medical image apparatus 100 may be implemented as one integrated controller, and the integrated controller may be included in only one of the workstation and the medical image apparatus 100. Hereinafter, the controller 200 may refer to the controller of the workstation and/or the controller of the medical image apparatus 100.

The output unit and the input unit of the workstation and the output unit 340 and the input unit 350 of the medical image apparatus 100 may each provide the user with an interface for manipulating the medical image apparatus 100. Each of the workstation and the medical image apparatus 100 may include an output unit and an input unit, but the present disclosure is not limited thereto. An output unit or an input unit may be implemented in only one of the workstation and the medical image apparatus 100.

Hereinafter, the input unit 350 refers to an input unit of the workstation and/or an input unit of the medical image apparatus 100, and the output unit 340 refers to an output unit of the workstation and/or an output unit of the medical image apparatus 100.

The input unit 350 may receive a command for manipulating the medical image apparatus 100 and various information about X-ray imaging from the user. The controller 200 may control or manipulate the medical image apparatus 100 based on information input through the input unit 350. Examples of the input unit 350 may include a joystick, a keyboard, a mouse, a touchscreen, an imaging button, a lock release button, a voice recognizer, a fingerprint recognizer, and an iris recognizer, and various other input devices apparent to one of ordinary skill in the art. The user may input a command for X-ray emission through the input unit 350, and a switch for inputting a command may be provided on the input unit 350. The switch may be provided to receive a command for X-ray emission only when the switch is pressed twice.

That is, the switch may have a structure in which when the user presses the switch, a preparation command for instructing preheating for X-ray emission is input, and when the switch is pressed deeper in this state, an emission command for actual X-ray emission is input. When the user manipulates the switch in this way, the controller 200 generates a signal corresponding to a command input through the switch manipulation, that is, a preparation signal, and transmits the preparation signal to the high voltage generator for generating a high voltage for X-ray generation.

The high voltage generator starts preheating by receiving the preparation signal from the controller 200, and when the preheating is completed, the high voltage generator transmits a preparation completion signal to the controller 200. For X-ray detection, the detector also needs to be prepared for X-ray detection. The controller 200 transmits the preparation signal to the detector so that the detector prepares to detect an X-ray transmitted through the object along with the preheating of the high voltage generator. When the detector receives the preparation signal, the detector prepares to detect an X-ray, and when detection preparation is completed, the detector transmits a detection preparation completion signal to the controller 200.

When the preheating of the high voltage generator is completed and the X-ray detection preparation of the detector is completed, the controller 200 transmits an emission signal to the high voltage generator, the high voltage generator generates a high voltage and applies the high voltage to an X-ray source, and the X-ray source emits an X-ray.

When the controller 200 transmits the emission signal, the controller 200 may transmit a sound or light output signal to the output unit 340 so that the object knows X-ray emission, and the output unit 340 may output certain sound or light. Also, the output unit 340 may output sound or light indicating other imaging-related information in addition to X-ray emission. The output unit 340 may be included in the manipulation unit, but the present disclosure is not limited thereto. The output unit 340 or a part of the output unit 340 may be located at a point different from a point where the manipulation unit is located. For example, the output unit 340 may be located on a wall of an imaging room where X-ray imaging of the object is performed.

The controller 200 controls positions of an X-ray emitter and the detector, an imaging timing, an imaging condition, etc. according to an imaging condition set by the user.

In detail, the controller 200 controls an X-ray emission timing, an intensity of an X-ray, and an emission area of an X-ray by controlling the high voltage generator and the detector according to a command input through the input unit 350. Also, the controller 200 adjusts a position of the detector according to a certain imaging condition, and controls an operation timing of the detector.

Also, the controller 200 generates a medical image of the object by using image data received through the detector. In detail, the controller 200 may receive image data from the detector, may remove noise of the image data, and may generate a medical image of the object by adjusting a dynamic range and interleaving.

The workstation may further include a communicator (not shown) that may be connected to a server, a medical device, and a portable terminal through a network.

Sliding of the detector arm 170 will be described.

Figure 4:
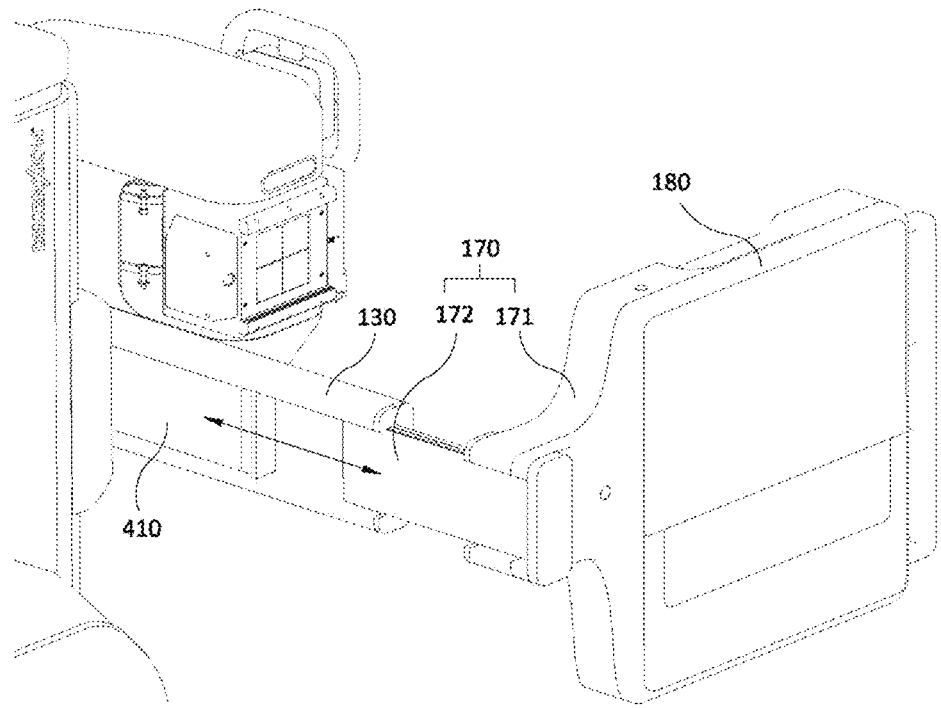
FIG. 4 is a view for describing a detector arm according to an embodiment of the present disclosure.

FIG. 4 is a view for describing a detector arm according to an embodiment of the present disclosure. Also, FIG. 5 is a view for describing a detector arm according to an embodiment of the present disclosure.

Figure 5:
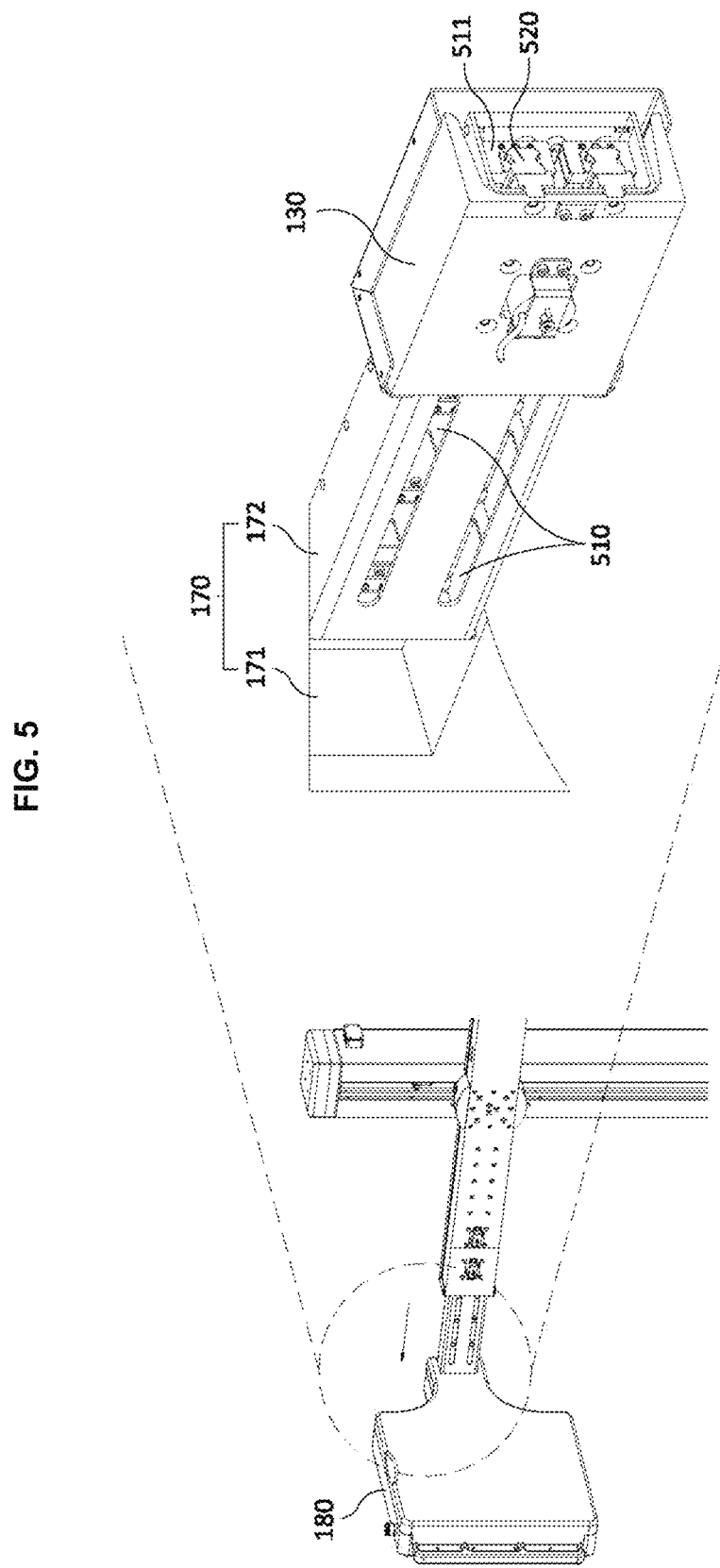
FIG. 5 is a view for describing a detector arm according to an embodiment of the present disclosure.

FIGS. 4 and 5 are views illustrating a medical image apparatus viewed in different directions.

Referring to FIGS. 4 and 5, the detector arm 170 may include a detector sliding portion 172 and a detector coupling portion 171. The detector sliding portion 172 may be parallel to a longitudinal direction of the straight arm 130. Also, the detector coupling portion 171 may be perpendicular to the straight arm 130 and may be coupled to the detector 180 to support the detector 180.

A guide hole 410 into which the detector sliding portion 172 is inserted may be formed in the straight arm 130. The detector sliding portion 172 of the detector arm 170 may be inserted into the guide hole 410 formed in the straight arm. Also, the detector sliding portion 172 may slide along the guide hole 410 formed in the straight arm 130. That is, the detector sliding portion 172 may slide in the longitudinal direction of the straight arm 130. However, the present disclosure is not limited thereto, and the straight arm 130 and the detector arm 170 may be coupled to each other in various ways. For example, the straight arm 130 may be inserted into a hole formed in the detector arm 170, and a plurality of rollers formed in the hole of the detector arm 170 may move by contacting a guide rail formed outside the straight arm 130.

At least one detector sliding groove 510 parallel to the longitudinal direction of the straight arm 130 may be formed in the detector sliding portion 172. Also, a guide rail groove 511 may be formed in the detector sliding portion 172. A sliding protrusion 520 may be formed in the straight arm. When the detector sliding portion 172 is inserted into the straight arm 130, the sliding protrusion 520 formed in the straight arm 130 may pass through the detector sliding groove 510 and may be engaged with the guide rail groove 511. That is, the sliding protrusion 520 formed in the straight arm 130 may pass through the detector sliding groove 510 and may be located in the detector arm 170. Because the sliding protrusion 520 formed in the straight arm 130 passes through the detector sliding groove 510 and is engaged with the guide rail groove 511, the detector arm 170 may slide along the straight arm 130 without shaking. This is because the sliding protrusion 520 is supported by the detector sliding groove 510 and the guide rail groove 511. Also, as shown in FIG. 4, the detector arm 170 may include a plurality of detector sliding grooves 510 and a plurality of guide rail grooves 511. Also, the straight arm 130 may include a plurality of sliding protrusions 520. Because the plurality of guide rail grooves 511 are engaged with the plurality of sliding protrusions 520, the straight arm 130 and the detector arm 170 may be more firmly coupled to each other, with little vibration and shaking. Although the detector arm 170 and the straight arm 130 are coupled to each other, this is merely an embodiment, and the detector arm 170 and the straight arm 130 may be coupled to each other in another embodiment.

As such, because the detector arm 170 is slidable in a direction of the straight arm 130, a distance between the detector 180 and the source assembly 160 may change.

The detector arm 170 may be moved by a detector driving unit. In the medical image apparatus 100, the detector arm 170 may be moved by the detector driving unit to be located at a first position. The first position may refer to a position of the detector arm 170 on the straight arm 130. When the detector arm 170 is located at the first position, a distance between the detector 180 and the source assembly 160 may be a first distance. For example, the first distance may be equal to or greater than 90 mm and equal to or less than 110 mm. In the medical image apparatus 100, the detector arm 170 may be moved by the detector arm driving unit to be located at a second position. The second position may refer to a position of the detector arm 170 on the straight arm 130. When the detector arm 170 is located at the second position, a distance between the detector 180 and the source assembly 160 may be a second distance. For example, the second distance may be equal to or greater than 120 mm and equal to or less than 140 mm. The first distance may be less than the second distance. In the medical image apparatus 100, when the detector arm 170 is located at the first position or at the second position, a medical image may be captured. In the present disclosure, the medical image may refer to at least one of a 2D, 2.5D, or 3D X-ray image, or a CT image.

Figure 6:
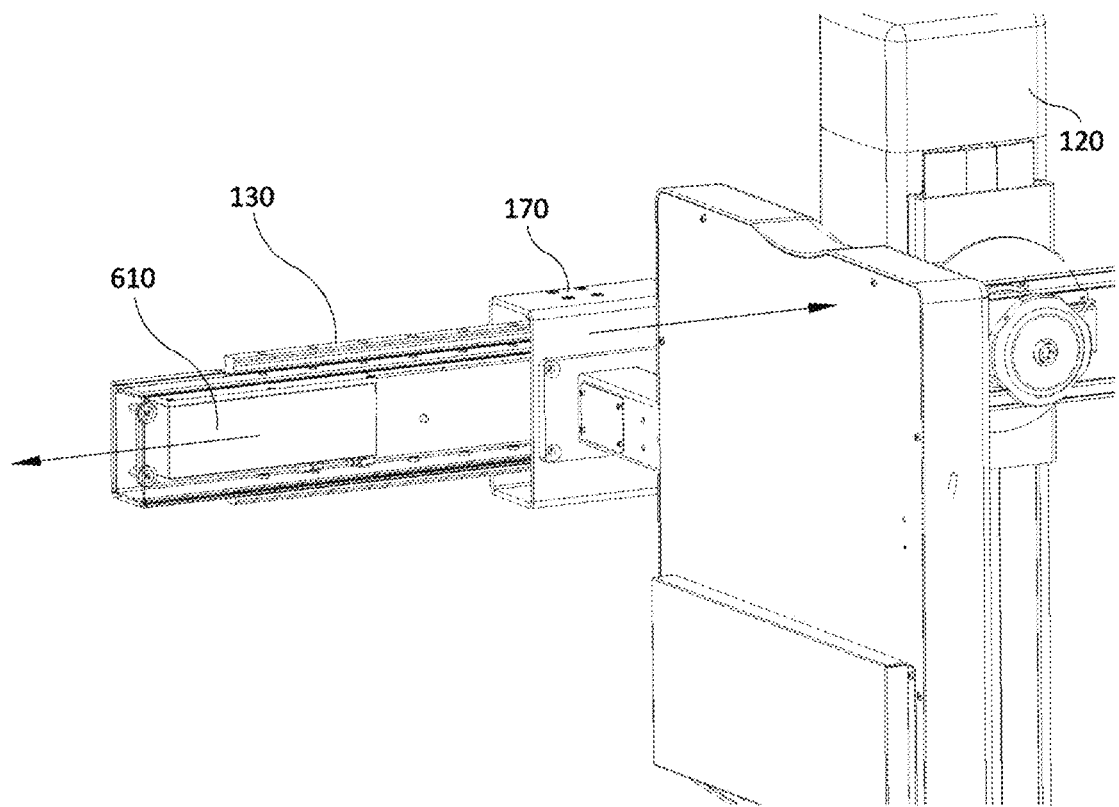
FIG. 6 is a view illustrating a medical image apparatus according to an embodiment of the present disclosure.

FIG. 6 is a view illustrating a medical image apparatus according to an embodiment of the present disclosure.

As described above, the detector arm 170 of the medical image apparatus 100 may move along the straight arm 130. In this case, because the source arm 150 is fixed, as the detector arm 170 moves, a position of the center of weights of the straight arm 130, the source arm 150, and the detector arm 170 may change. Although the center of weights changes, when a user who does not know the change releases locking in order to rotate the straight arm 130 with respect to the column 120, the straight arm 130 may suddenly move. This is because in the straight arm 130, a heavy side tends to move downward.

Accordingly, the medical image apparatus 100 may include a straight arm balance weight 610. The straight arm 130 may include a straight arm weight moving hole formed in a longitudinal direction. The straight arm balance weight 610 may be located in the straight arm weight moving hole. However, the present disclosure is not limited thereto, and the straight arm balance weight 610 may be located outside the straight arm 130. Also, the straight arm balance weight 610 may be located inside the detector arm 170 or may be located outside the detector arm 170.

The straight arm balance weight 610 may slide in the longitudinal direction of the straight arm 130. The straight arm balance weight 610 may move in a direction opposite to a sliding direction of the detector arm 170. When the detector arm 170 slides, the straight arm balance weight 610 may also slide. Although the medical image apparatus 100 separately includes a driving unit for the straight arm balance weight 610, the present disclosure is not limited thereto. The straight arm balance weight 610 may interoperate with a detector driving unit and may move simultaneously with the detector arm 170. When the detector arm 170 slides rightward or leftward, the straight arm balance weight 610 may slide leftward or rightward. As such, when the detector arm 170 moves with respect to the straight arm 130, the straight arm balance weight 610 also moves with respect to the straight arm 130. Accordingly, a position of the center of weights of the straight arm 130, the source arm 150, and the detector arm 170 may always be constant.

Also, when the detector arm 170 moves, the medical image apparatus 100 may undergo a reaction to acceleration of the detector arm 170. Accordingly, vibration or trembling may occur in the medical image apparatus, which may affect imaging or may affect the durability of the medical image apparatus 100 in some cases. However, according to the medical image apparatus 100 of the present disclosure, because the detector arm 170 and the straight arm balance weight 610 simultaneously move in opposite directions, the medical image apparatus 100 may not be shaken and durability may be increased.

Figure 7:
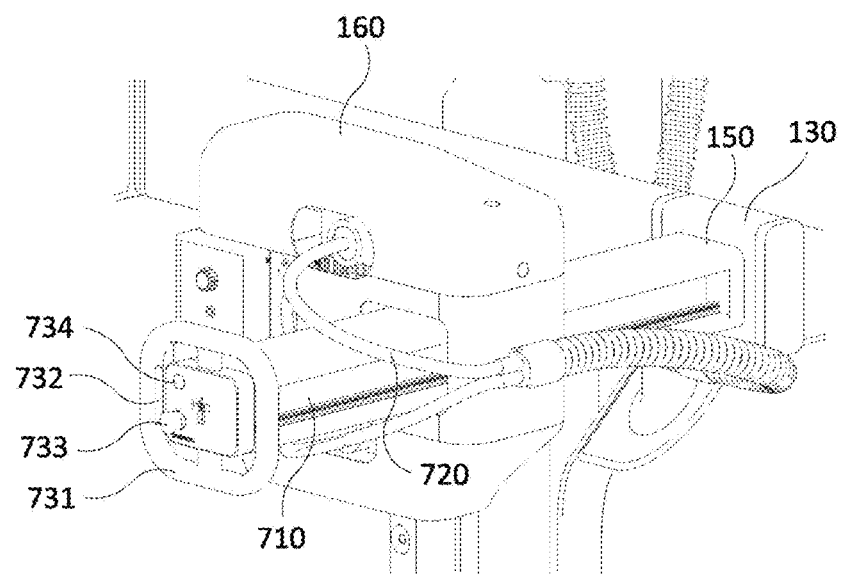
FIG. 7 is a view for describing a source arm according to an embodiment of the present disclosure.

FIG. 7 is a view for describing a source arm according to an embodiment of the present disclosure.

The source arm 150 may pass through a hole formed in the source assembly 160. A hole 720 may be formed in the source assembly 160. Also, at least one roller (not shown) may be formed in the hole of the source assembly 160. A source driving rail 710 may be formed on the source arm 150. According to FIG. 7, the source driving rail 710 may be formed on a side of the source arm 150 in a longitudinal direction of the source arm 150. However, the present disclosure is not limited thereto, and the source driving rail 710 may be formed on both sides of the source arm. Also, the source driving rail 710 may be formed inside the source arm, instead of on an outer surface of the source arm, thereby preventing the accident of being caught between the source driving rail 710 and the roller. Because the medical image apparatus is used in a hospital, safety may be essential. The roller formed in the hole 720 of the source assembly 160 may contact the source driving rail 710. That is, the roller located in the hole 720 of the source assembly 160 may be engaged with the source driving rail 710 of the source arm 150. The source assembly 160 may slide along the source driving rail 710 formed on the source arm 150.

A handle 731 may be formed on a front end of the source arm 150. The handle 731 may have a shape surrounding a cross-section of the source arm 150. The handle 731 may have a shape surrounding a cross-section perpendicular to the longitudinal direction of the source arm 150. Because the handle 731 is formed on an end of the source arm 150, a user may rotate the straight arm 130 at a position not colliding with the source arm 150 or the detector arm 170. Accordingly, the safety of the medical image apparatus 100 may be improved. Also, because the handle 731 has a shape surrounding a cross-section of the source arm 150, the user may comfortably manipulate the medical image apparatus with his left hand or right hand. Even when the user is located on the left or the right of the medical image apparatus 100, the user may manipulate the medical image apparatus.

A lock release button 732 may be located on an end of the source arm 150. The lock release button 732 may be a button for determining whether to rotate the straight arm 130 with respect to the column 120. When the user is to rotate the straight arm 130, the user may press the lock release button 732 and may rotate the straight arm 130. When the lock release button 732 is pressed, the straight arm 130 may be rotatable. However, the present disclosure is not limited thereto, and the straight arm 130 may be rotatable only when an additional condition is further satisfied.

The medical image apparatus 100 may control rotation of the straight arm 130 by using an electromagnetic brake. When the lock release button is not pressed, a brake pad and a ground surface formed on the straight arm 130 or the straight arm moving unit 140 may contact and thus the electromagnetic brake may prevent rotation of the straight arm 130. When the lock release button 732 is pressed, the medical image apparatus 100 may transmit an electrical signal to the electromagnetic brake, and when the brake pad is separated from the ground surface by an electromagnet, locking may be released.

The source arm 150 may include an emergency button 733. When an accident may occur, the emergency button 733 may be pressed by the user. When the emergency button 733 is pressed, the medical image apparatus 100 may stop a wheel of the main body 110. That is, when the medical image apparatus 100 is likely to collide with a person or a wall, the user may press the emergency button 733, and the medical image apparatus 100 may suddenly brake the wheel of the main body 110, thereby preventing damage due to collision. Also, even if the user does not intentionally press the emergency button 733, when the medical image apparatus 100 moves forward and collides with an obstacle, the emergency button 733 located at the front may be pressed and additional damage to the obstacle or the medical image apparatus 100 may be avoided. Additionally, when the emergency button 733 is pressed, the medical image apparatus 100 may stop at least one of movement of the source assembly 160, movement of the detector arm 170, vertical movement of the straight arm 130, or rotation of the straight arm 130, to prevent an emergency.

The source arm 150 may include a sensor 734. The sensor 734 may be a forward collision avoidance sensor. The forward collision avoidance sensor may be a sensor for detecting whether there is a solid object in a non-contact manner. The forward collision avoidance sensor may be a sensor for measuring a distance to a solid object ahead. Examples of the forward collision avoidance sensor may include an ultrasonic sensor, an infrared sensor, a LIDAR sensor, a RADAR sensor, a camera sensor, or a laser sensor. The forward collision avoidance sensor may detect an obstacle located in front of the medical image apparatus 100. Also, when the medical image apparatus 100 receives information indicating that there is an obstacle ahead from the forward collision avoidance sensor, the medical image apparatus 100 may decelerate or stop the wheel of the main body 110.

Various coupling methods of the source arm 150 and the source assembly 160 will be described.

Figure 8:
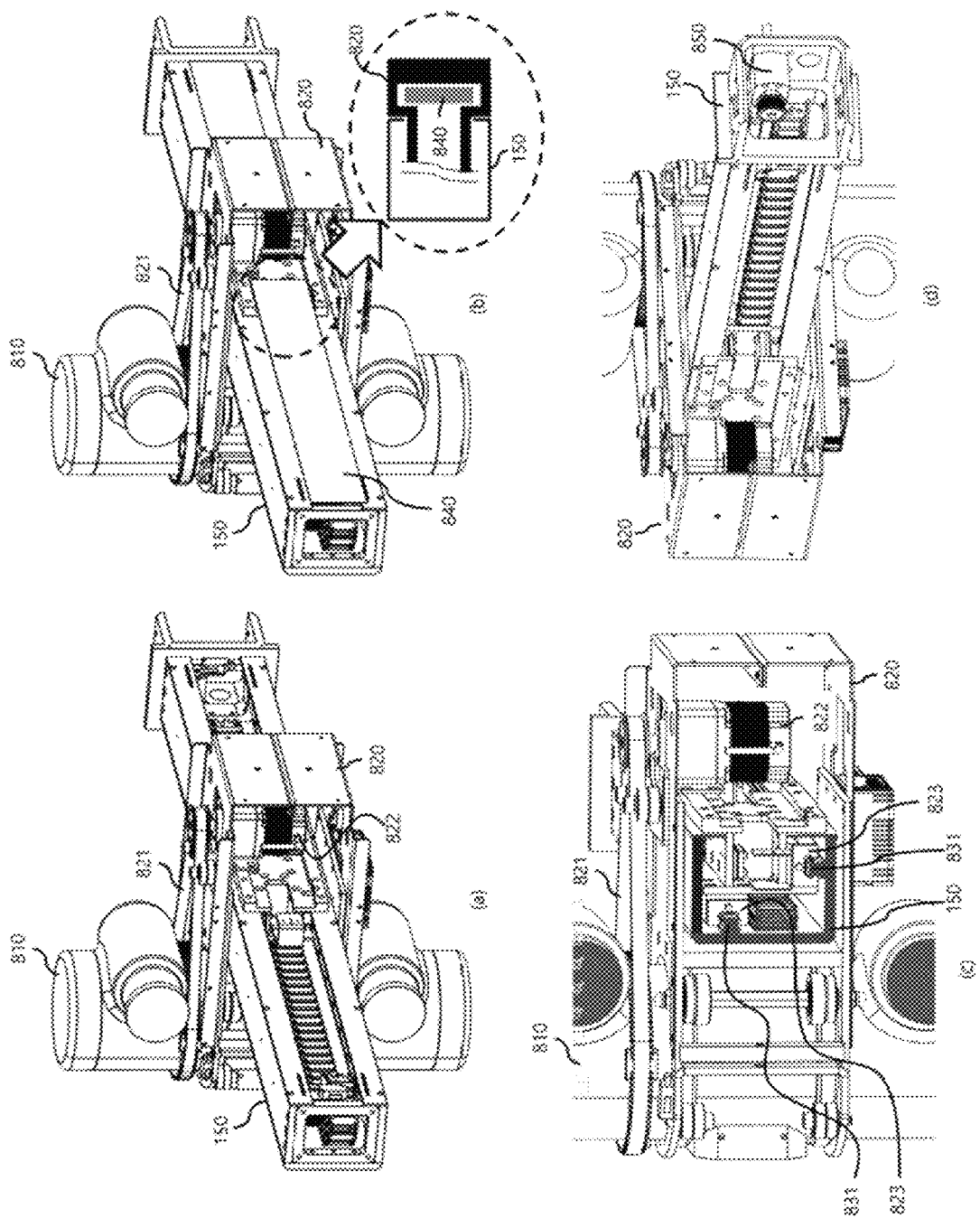
FIG. 8 is a view illustrating a source arm and a source assembly according to an embodiment of the present disclosure.

FIG. 8 is a view illustrating a source arm and a source assembly according to an embodiment of the present disclosure.

FIG. 8 is a view in which a housing of the source assembly 160 is removed to describe the source assembly 160 and the source arm 150.

Referring to (a) of FIG. 8, the source assembly 160 may include a source 810 and a source assembly driving unit 820. The source 810 may be an element for generating an X-ray. Although FIG. 8 illustrates only the source 810, a collimator for controlling an X-ray of the source 810 to be emitted to a specific area may be further included. Also, the source assembly driving unit 820 may be an element for rotating the source 810 or moving the source assembly 160 on the source arm 150.

The medical image apparatus 100 may control the source 810 to face the detector 180 in order to capture a medical image of an object. In more detail, the medical image apparatus 100 may control the source 810 to face the center of the detector 180. As described above, the source assembly 160 may move in a longitudinal direction of the source arm on the source arm 150. Accordingly, the medical image apparatus 100 may obtain a 2D, 2.5D, or 3D image of the object. In order to cause the source 810 to face the center of the detector 180 while the source assembly 160 moves along the source arm 150, the medical image apparatus 100 may have to rotate the source 810. Also, the detector arm 170 may move along the straight arm 130, and as the detector arm 170 moves, a distance between the detector 180 and the source assembly 160 may change. Also, when the distance between the detector 180 and the source assembly 160 changes, the medical image apparatus 100 may have to rotate the source 810 so that the source 810 faces the center of the detector 180.

In order to rotate the source 810, the source assembly driving unit 820 included in the source assembly 160 may include a source rotation actuator 822. The source rotation actuator 822 may be driven based on a control signal of the controller 300. A source rotation belt 821 may be wound around an outer surface of the source 810 and a rotating shaft of the source rotation actuator 822. A driving force of the source rotation actuator 822 may be transmitted to the source 810 based on the source rotation belt 821. The controller 300 may determine a control signal transmitted to the source rotation actuator 822 based on a position of the source assembly 160 on the source arm 160 and a distance between the detector 180 and the source assembly 160. Accordingly, the source 810 may face the detector 180, and the medical image apparatus 100 may obtain a clear medical image of the object.

As such, because the source 810 is located on a side of the source arm 150 based on the source arm 150 and a part of the source assembly driving unit 820 is located on the other side of the source arm 150, excessive load on the side or the other side of the source arm 150 may be prevented. Also, because the center of weights of the source 810 and the source assembly driving unit 820 is located in the source arm 150, the burden on the source arm 150 may be reduced. Also, in this configuration, when the source assembly 160 moves along the source arm 150, shaking may be small. Accordingly, the medical image apparatus 100 may obtain a clear medical image.

Referring to (b) of FIG. 8, the source arm 150 may include a source arm cover 840. A side surface of the source arm 150 may be open so that a source guide groove 823 of the source assembly driving unit 820 extends into the source arm 150. The source arm cover 840 may be an element for covering the open side surface of the source arm 150. Because the side surface of the source arm 150 is covered by the source arm cover 840, an outer appearance may become neat, and an accident in which a solid object is caught between the source arm 150 and the source assembly 160 may be prevented.

(c) of FIG. 8 illustrates cross-sections of the source arm 150 and the source assembly 160. Referring to (c) of FIG. 8, the source arm 150 may include at least one source arm guide protrusion 831 therein. Referring to (c) of FIG. 8, the source arm guide protrusion 831 may be formed on a bottom surface in the source arm. Also, referring to (c) of FIG. 8, the source arm guide protrusion 831 may be formed on a side surface in the source arm. The source arm guide protrusion 831 may extend in the longitudinal direction of the source arm 150. The source arm guide protrusion 831 may be an element for guiding the source assembly 160 to move along the source arm 150.

The source assembly 160 may include the source guide groove 823. The source guide groove 823 may be engaged with the source arm guide protrusion 831. The number of the source guide grooves 823 may be equal to the number of the source arm guide protrusions 831.

Also, the source arm guide protrusion 831 may be engaged with the source guide groove 823, so that the source assembly 160 is not shaken while moving along the source arm 150. Also, as shown in (c) of FIG. 8, two source arm guide protrusions 831 may be provided, and the source assembly 160 may stably move along the source arm 150 without shaking. Also, referring to (c) of FIG. 8, because the source arm guide protrusions 831 are located on a side surface and a bottom surface of the source arm 150 and the source guide grooves 823 are formed to correspond to the source arm guide protrusions 831, even when the straight arm 130 rotates with respect to the column 120, the source assembly 160 may be firmly coupled to the source arm 150. Also, even when the straight arm 130 has an angle of 0° to 90° with respect to the ground, the source assembly 160 may move along the source arm 150 without shaking.

In order for the medical image apparatus 100 to obtain a clear medical image, it is essential that the source assembly 160 moves along the source arm 150 without shaking. Because the medical image apparatus 100 according to the present disclosure includes at least one source arm guide protrusion 831 and at least one source guide groove 823, the source assembly 160 may move along the source arm 150 without shaking, and the medical image apparatus 100 may obtain a clear medical image.

(d) of FIG. 8 is a view of (c) of FIG. 8 viewed at a different angle. Referring to (d) of FIG. 8, the source arm 150 or the straight arm 130 may include a source arm sliding actuator 850. The source sliding actuator 850 may be driven based on a control signal of the controller 300. A rotating shaft of the source arm sliding actuator 850 may be connected to the source assembly 160 via a belt or a line. When the source arm sliding actuator 850 rotates in one direction, the source assembly 160 may move farther away from the straight arm 130. Also, when the source arm sliding actuator 850 rotates in the other direction, the source assembly 160 may move closer to the straight arm 130.

The straight arm moving unit 140 will be described in more detail.

Figure 9:
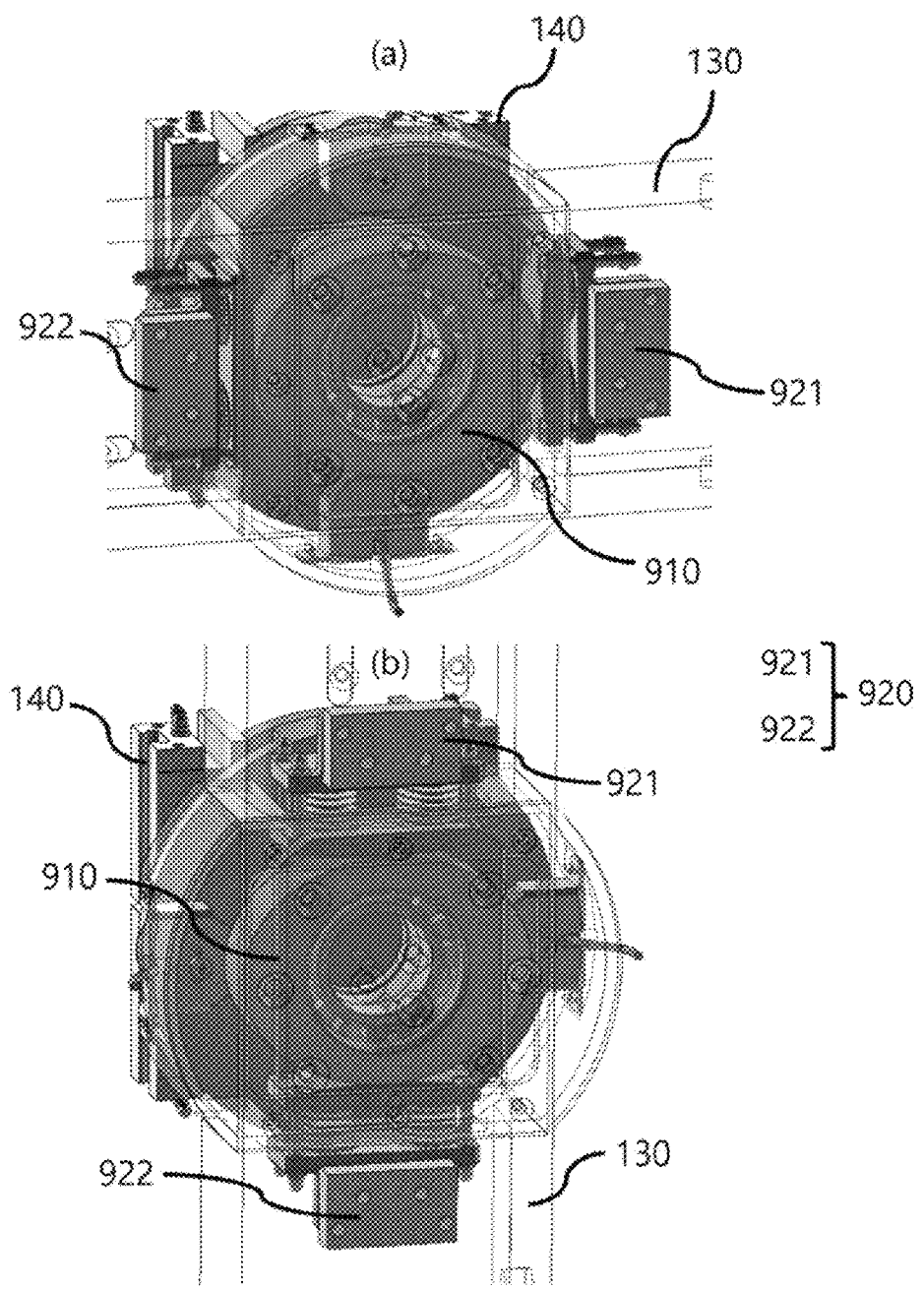
FIG. 9 is a view illustrating a straight arm rotating unit according to an embodiment of the present disclosure.
Figure 10:
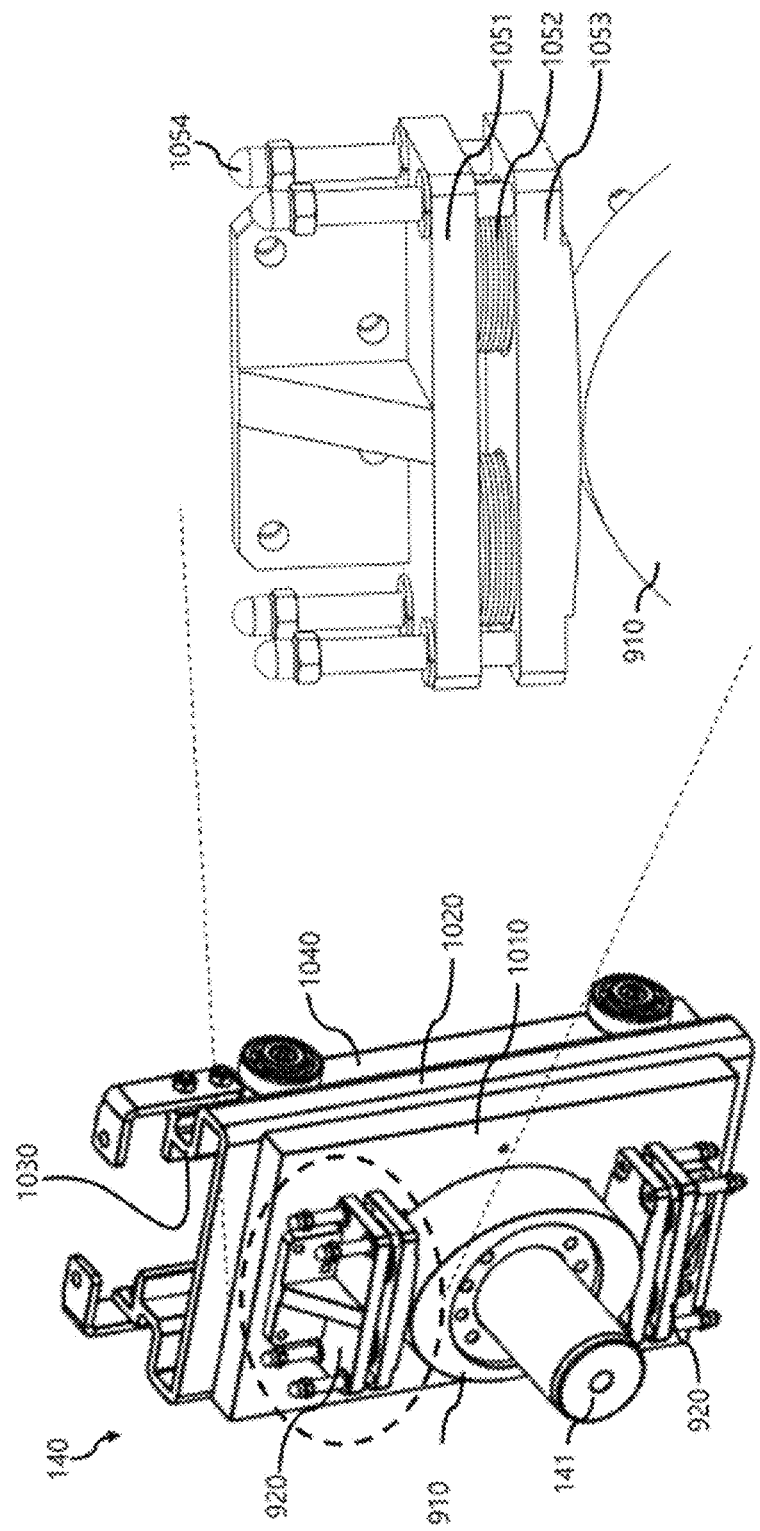
FIG. 10 is a view illustrating a straight arm rotating unit viewed from a viewpoint according to an embodiment of the present disclosure.
Figure 11:
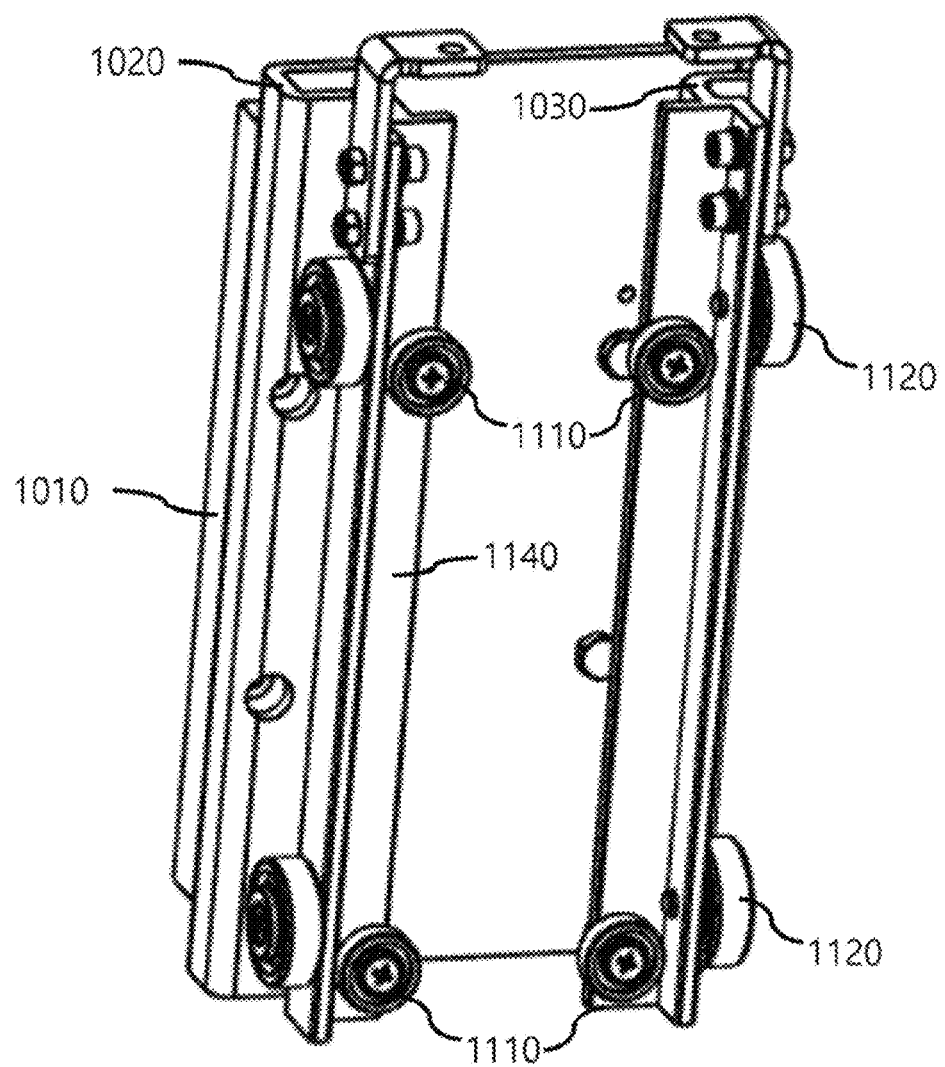
FIG. 11 is a view illustrating a straight arm rotating unit viewed from another viewpoint according to an embodiment of the present disclosure.

FIG. 9 is a view illustrating a straight arm rotating unit according to an embodiment of the present disclosure. Also, FIG. 10 is a view illustrating a straight arm rotating unit viewed from one viewpoint according to an embodiment of the present disclosure. FIG. 11 is a view illustrating a straight arm rotating unit viewed from another viewpoint according to an embodiment of the present disclosure.

In FIGS. 9, 10, and 11, for convenience of explanation, some elements of the medical image apparatus 100 are omitted or are made transparent. Referring to FIG. 9, the medical image apparatus 100 may include the straight arm 130 and the straight arm moving unit 140. The straight arm 130 may include a balance unit 920. The balance unit 920 may include a first balance unit 921 and a second balance unit 922. Also, the straight arm moving unit 140 may include a camshaft 910. When viewed from the front of the medical image apparatus 100, the camshaft may have an elliptical shape. The first balance unit 921 and the second balance unit 922 may face each other, and the camshaft 910 may be located between the first balance unit 921 and the second balance unit 922.

According to another embodiment of the present disclosure, the straight arm moving unit 140 may include the balance unit 920. That is, the balance unit 920 may be fixed to the straight arm moving unit 140. The balance unit 920 may include the first balance unit 921 and the second balance unit 922. Also, the straight arm 130 may include the camshaft 910. That is, the camshaft 910 may be fixed to the straight arm 130. When the straight arm moving unit 140 includes the balance unit 920, the straight arm 130 may include the camshaft 910, and when the straight arm moving unit 140 includes the camshaft 910, the straight arm 130 may include the balance unit 920.

Rotation of the straight arm 130 may be limited by a shape of the camshaft 910. For example, as shown in FIG. 9, a longer radius of the camshaft 910 may be parallel to the ground. However, the present disclosure is not limited thereto, and a longer radius of the camshaft may be perpendicular to the ground. As shown (a) of FIG. 9, when a longer radius of the camshaft 910 is parallel to the ground and the straight arm 130 is parallel to the ground, the balance unit 920 of the straight arm 130 may be compressed. Also, as shown in (b) of FIG. 9, when a longer radius of the camshaft 910 is parallel to the ground and the straight arm 130 is perpendicular to the ground, the balance unit 920 of the straight arm 130 may not be compressed. Accordingly, in order for the user to make the straight arm 130 horizontal in a state where the straight arm 130 is vertical, strong force may have to be applied. Also, in order for the user to make the straight arm 130 vertical in a state where the straight arm 130 is horizontal, the straight arm 130 may naturally rotate even without applying a strong force.

In contrast, when a longer radius of the camshaft 910 is perpendicular to the ground, in order for the user to make the straight arm 130 vertical in a state where the straight arm 130 is horizontal, a strong force may have to be applied. Also, in order for the user to make the straight arm 1320 horizontal in a state where the straight arm 130 is vertical, the straight arm 130 may naturally rotate even without applying a strong force. As such, because the medical image apparatus 100 limits rotation of the straight arm 130, a situation where the straight arm 130 suddenly rotates and a patient or a user collides with the straight arm 130, the source arm 150, or the detector arm 170 may be prevented.

Structures of the straight arm 130 and the straight arm moving unit 140 will be described in more detail with reference to FIGS. 10 and 11.

FIGS. 10 and 11 illustrate a configuration according to an embodiment of the present disclosure, but the present disclosure is not limited thereto.

Referring to FIGS. 10 and 11, the straight arm moving unit 140 may slide in a longitudinal direction of the column 120. Also, the straight arm moving unit 140 may include the moving unit rotating shaft 141 for rotating the straight arm 130. The moving unit rotating shaft 141 may be fixed to the straight arm moving unit 140. A rotating shaft groove may be formed in the straight arm 130 and the moving unit rotating shaft 141 may be inserted into the rotating shaft groove of the straight arm 130. The straight arm 130 may rotate about the moving unit rotating shaft 141.

The straight arm moving unit 140 may include the camshaft 910. The camshaft 910 may be formed along a side surface of the moving unit rotating shaft 141. In more detail, the camshaft 910 may surround the side surface of the moving unit rotating shaft 141. Also, the camshaft 910 may be integrally formed with the moving unit rotating shaft 141. However, the present disclosure is not limited thereto. A hole may be formed at the center of the camshaft 910. Also, the moving unit rotating shaft 141 may be coupled by being inserted into the hole formed in the camshaft 910. The camshaft 910 may have an elliptical cross-sectional shape. In more detail, the camshaft 910 may have an elliptical shape when viewed from the front of the medical image apparatus 100. The camshaft 910 may be fixed to the straight arm moving unit.

The straight arm moving unit 140 may include a base portion 1010. The base portion 1010 may be coupled to the moving unit rotating shaft 141 and may have a surface perpendicular to the moving unit rotating shaft 141. The base portion 1010 may also be coupled to the camshaft 910.

Also, the straight arm moving unit 140 may include a convex portion 1020. The convex portion 1020 may have a convex shape with respect to left and right sides of the base portion 1010. The convex portion 1020 may be connected to both sides of the base portion 1010. The convex portion 1020 may be an element for supporting both sides of a front cover of the column 120. Also, the convex portion 1020 may extend vertically.

The straight arm moving unit 140 may include a concave portion 1030. The concave portion 1030 may have a concave shape with respect to left and right sides of the base portion 1010 or the convex portion 1020. The concave portion 1030 may be connected to both sides of the convex portion. The concave portion 1030 may be engaged with an open portion of the column 120. The open portion of the column 120 may be moving unit rails 1223, 1224. The concave portion 1030 may be engaged with a blade 1210 of the open portion of the column 120. The concave portion 1030 may extend vertically.

Also, the straight arm moving unit 140 may include a roller connecting portion 1040. The roller connecting portion 1040 may be connected to the concave portion 1030. The roller connecting portion 1040 may extend vertically, and may be an element for coupling rollers 1110, 1120. The straight arm moving unit 140 may include a plurality of rollers 1110, 1120. A roller rotating shaft coupled to the roller connecting portion 1040 may extend in a left-right direction or may extend in a front-back direction. The plurality of rollers 1110, 1120 may include the roller 1110 rotating based on a roller rotating shaft extending in a front-back direction and the roller 1120 rotating based on a roller rotating shaft extending in a left-right direction. For example, the straight arm moving unit 140 may include four rollers 1110 and four rollers 1120. However, the present disclosure is not limited thereto.

An electromagnet or a permanent magnet may be formed on a surface where the straight arm moving unit 140 and the column 120 face each other. An electromagnet or a permanent magnet may be formed on a surface of the straight arm moving unit 140, and a permanent magnet or an electromagnet may be formed on a surface of the column 120. When the medical image apparatus 100 is to stop vertical movement of the straight arm moving unit 140, a polarity of the electromagnet or the permanent magnet formed on the straight arm moving unit 140 may be different from a polarity of the permanent magnet or the electromagnet formed on the surface of the column 120. That is, due to the attractive force of the magnet, the surface of the column may be coupled to the surface of the straight arm moving unit 140. Due to friction between the surface of the column 120 and the surface of the straight arm moving unit 140, the straight arm moving unit 140 may be firmly stopped. When the medical image apparatus 100 is to vertically move the straight arm moving unit 140, a polarity of the electromagnet or the permanent magnet formed on the straight arm moving unit 140 may be the same as a polarity of the permanent magnet or the electromagnet formed on the surface of the column 120. That is, due to a repulsive force, the surface of the column 120 and the surface of the straight arm moving unit 140 may be pushed away from each other. Because the surface of the column 120 and the surface of the straight arm moving unit 140 do not meet each other, the straight arm moving unit 140 may move without friction.

Referring to FIG. 10, the balance unit 920 may include the first balance unit 921 and the second balance unit 922. The balance unit 920 may be fixed to the straight arm 130 and may contact a side surface of the camshaft 910. Also, the balance unit 920 may press the side surface of the camshaft 910 due to an elastic body 1052. In more detail, the balance unit 920 may press the side surface of the camshaft 910 in a radial direction of the camshaft 910.

The balance unit 920 may include a balance fixing portion 1051. The balance unit 920 may be coupled to the straight arm 130 or the straight arm moving unit 140 due to the balance fixing portion 1051. As described above, when the balance unit 920 is fixed to the straight arm moving unit 140, the camshaft 910 may be fixed to the straight arm 130. Also, when the camshaft 910 is fixed to the straight arm moving unit 140, the balance unit 920 may be fixed to the straight arm 130.

The balance unit 920 may include a camshaft pressing portion 1053. The camshaft pressing portion 1053 may contact the camshaft 910 and may be an element for pressing the side surface of the camshaft 910. The balance fixing portion 1051 and the camshaft pressing portion 1053 may be coupled to each other by a fixing screw 1054.

Also, the balance unit 920 may include the elastic body 1052. The elastic body 1052 may be located between the balance fixing portion 1051 and the camshaft pressing portion 1053. Due to the elastic body 1052, the camshaft pressing portion 1053 may contact the camshaft 910 and may apply a force to the camshaft 910. The balance fixing portion 1051 may be fixed to the straight arm 130 or the straight arm moving unit 140, and the camshaft pressing portion 1053 may receive a force from the elastic body 1052 and may apply a force to the camshaft 910. In more detail, the first balance unit 921 may press a side of the camshaft 910, and the second balance unit 922 may press the other side of the camshaft 910. As such, rotation of the straight arm 130 may be limited by a shape of the camshaft 910 and the balance unit 920. Also, because the medical image apparatus 100 limits rotation of the straight arm 130, a situation where the straight arm 130 suddenly rotates and a patient or a user collides with the straight arm 130, the source arm 150, or the detector arm 170 may be prevented.

Figure 12:
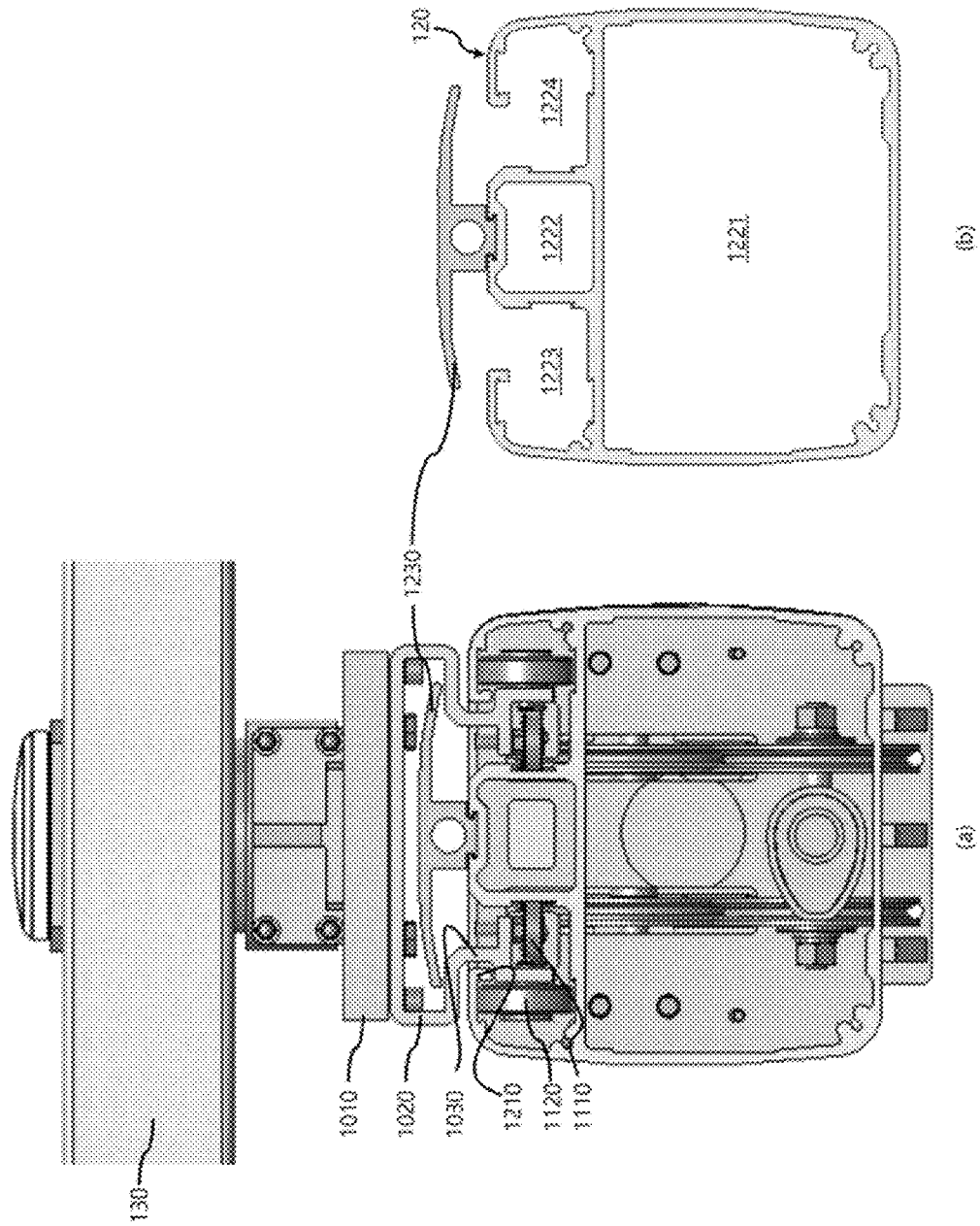
FIG. 12 is a cross-sectional view for describing a column according to an embodiment of the present disclosure.

FIG. 12 is a cross-sectional view for describing a column according to an embodiment of the present disclosure.

FIG. 12 illustrates a cross-section of the column 120 viewed from the bottom of the medical image apparatus 100. (a) of FIG. 12 illustrates not only the column 120 but also the straight arm 130 and the straight arm moving unit 140 and (b) of FIG. 12 illustrates a cross-section of the column 120. In (b) of FIG. 12, elements other than the column 120 are omitted to describe the column 120.

Referring to (a) and (b) of FIG. 12, the column 120 may include a first space portion 1221. The first space portion 1221 may extend in a longitudinal direction of the column in the column. The first space portion 1221 may be a space for a straight arm driving unit. The first space portion 1221 may be a space for arranging at least one of a gear, a weight, a pulley, or a pulley cord included in the straight arm driving unit.

The column 120 may include a second space portion 1222. The second space portion 1222 may extend in the longitudinal direction of the column in the column 120, and may be formed in front of the first space portion 1221. The second space portion 1222 may have a smaller cross-section than the first space portion 1221. Also, a front outer surface of the second space portion 1222 may include a groove for coupling a column cover 1230.

The moving unit rails 1223, 1224 may be formed on both sides of the second space portion. The plurality of rollers 1110, 1120 formed on both sides of or behind the straight arm moving unit 140 may vertically move along the moving unit rails 1223, 1224 formed in the column 120. In more detail, the moving unit rails 1223, 1224 may be formed on both sides of the second space portion 1222 and may contact the rollers 1110, and the rollers 1110 may move along the moving unit rails 1223, 1224. Also, the moving unit rails 1223, 1224 may be formed on an inner surface of the column 120 and may contact the rollers 1120, and the rollers 1120 may move along the moving unit rails 1223, 1224.

The medical image apparatus 100 may include the column cover 1230. The column cover 1230 may cover the moving unit rails 1223, 1224. The column cover 1230 may extend vertically.

As described above, the straight arm moving unit 140 may include the convex portion 1020. The convex portion 1020 may have a convex shape with respect to left and right sides of the base portion 1010. The convex portion 1020 may be connected to both sides of the base portion 1010. The convex portion 1020 may be an element for supporting both sides of a front cover of the column 120. Also, the convex portion 1020 may extend vertically. Also, the straight arm moving unit 140 may include the concave portion 1030. The concave portion 1030 may have a concave shape with respect to left and right sides of the base portion 1010 or the convex portion 1020. The concave portion 1030 may be connected to both sides of the convex portion. The concave portion 1030 may be engaged with an open portion of the column 120. The open portion of the column 120 may be the moving unit rails 1223, 1224. The concave portion 1030 may be engaged with the blade 1210 of each of the moving unit rails 1223, 1224 of the column 120. The concave portion 1030 may extend vertically.

FIG. 13 is a view illustrating a structure of a column according to various embodiments of the present disclosure.

A cross-section of the column 120 of FIG. 13 may have a shape different from that of a cross-section of the column 120 of FIG. 12. However, the column 120 of FIG. 12 may also be implemented based on a frame having a first shape and a frame having a second shape described in FIG. 13.

The column 120 may include frames 1311, 1312 having a first shape and a frame 1320 having a second shape, and the frames 1311, 1312 may have the first shape as shown in FIG. 13. A cross-section of each of the frames 1311, 1312 may include at least one closed portion and at least one open portion. The frame 1311 may have the same shape as that of the frame 1312. The frames 1311, 1312 may be formed through extrusion molding. The frame 1311 may have a mirror image of the frame 1312. The frame 1312 may be implemented with the top of the frame 1311 as the bottom of the frame 1312, and with the bottom of the frame 1311 as the top of the frame 1312. That is, the frames 1311, 1312 may have the same first shape.

The open portion formed in the frames 1311, 1312 may be used to couple the straight arm moving unit 140. A moving unit rail may be formed in the open portion formed in the frames 1311, 1312. A roller of the straight arm moving unit 140 may contact the moving unit rail in the open portion formed in the frames 1311, 1312 and may move along the moving unit rail.

A shape of the frames 1311, 1312 is not limited to that in FIG. 13. A half of the second space portion 1222 and the moving unit rail 1223 of the column 120 of FIG. 12 may correspond to the frame 1311. That is, a cross-section of the frame 1311 may have the same shape as that of a cross-section of the half of the second space portion 1222 and the moving unit rail 1223 of the column 120 of FIG. 12. Also, the remaining half of the second space portion 1222 and the moving unit rail 1224 of the column 120 of FIG. 12 may correspond to the frame 1312. That is, a cross-section of the frame 1312 may have the same shape as that of a cross-section of the remaining half of the second space portion 1222 and the moving unit rail 1224 of the column 120 of FIG. 12.

The frame 1320 may have the second shape as shown in FIG. 13. A cross-section of the frame 1320 may include at least one closed portion. An empty space of the frame 1320 may be a space for arranging at least one of a gear, a weight, a pulley, or a pulley cord included in a straight arm driving unit.

A shape of the frame 1320 is not limited to that in FIG. 13. The first space portion 1221 in the column 120 of FIG. 12 may correspond to the frame 1320. That is, the frame 1320 may have the same cross-section as that of the first space portion 1221 of the column 120 of FIG. 12.

The column 120 may be formed by coupling the frames 1311, 1312 having the first shape to the frame 1320 having the second shape. The two frames 1311, 1312 having the first shape included in the column 120 may be located in front of the frame 1320 having the second shape included in the column 120 to be coupled to the frame 1320 having the second shape.

The two frames 1311, 1312 having the first shape and the frame 1320 having the second shape may be coupled to each other by using an adhesive. Alternatively, the two frames 1311, 1312 having the first shape and the frame 1320 having the second shape may be welded to each other. Alternatively, the two frames 1311, 1312 having the first shape and the frame 1320 having the second shape may be coupled to each other by a housing surrounding all of the two frames 1311, 1312 having the first shape and the frame 1320 having the second shape. That is, the two frames 1311, 1312 having the first shape and the frame 1320 having the second shape may be inserted into the housing, and thus, the two frames 1311, 1312 having the first shape and the frame 1320 having the second shape may be coupled to each other.

Also, the source arm 150 and the detector arm 170 may include a frame having a first shape. Also, the straight arm 130 may include a frame having a second shape. As such, because all of the column 120, the straight arm 130, the source arm 150, and the detector arm 170 may be implemented by using only a frame having a first shape and a frame having a second shape, productivity may be improved and production cost may be reduced. Also, because a structure of the medical image apparatus 100 is simplified, maintenance of the medical image apparatus 100 may be facilitated.

FIG. 14 illustrates a medical image apparatus according to various embodiments of the present disclosure.

A column of the medical image apparatus 100 of FIG. 14 may have a structure different from that of a column of the medical image apparatus 100 of FIG. 1. However, the medical image apparatus 100 of FIG. 14 may perform the same function as the medical image apparatus 100 of FIG. 1. In the medical image apparatus 100 of FIG. 14, the column 120 may include a first column 1411, a second column 1412, and a column connecting portion 1413. Because the first column 1411 and the second column 1412 support the straight arm moving unit 140 on both sides, the straight arm moving unit 140 may be firmly fixed to the column 120. Also, when the medical image apparatus 100 travels, because a user's field of view is secured between the first column 1411 and the second column 1412, the driving safety of the medical image apparatus 100 may be increased. FIG. 14 will be described in more detail.

The column 120 may include the first column 1411. The first column 1411 may vertically extend and may be coupled to a left side of the main body 110. The column 120 may include the second column 1412. The second column 1412 may vertically extend and may be coupled to a right side of the main body 110. The column 120 may include the column connecting portion 1413. The column connecting portion 1413 may connect an upper portion of the first column 1411 to an upper portion of the second column 1412. A lower portion of the first column 1411 and a lower portion of the second column 1412 may be connected to each other by the main body 110. Accordingly, even when the source arm 150 or the straight arm 130 moves, the first column 1411 and the second column 1412 may hardly be shaken.

A moving unit rail for moving a roller of the straight arm moving unit 140 may be formed on the right of the first column 1411 and the left of the second column 1412. A plurality of rollers may be formed on both sides of the straight arm moving unit 140. A plurality of rollers that may move along the moving unit rail formed on the first column 1411 may be formed on the left of the straight arm moving unit 140. Also, a plurality of rollers that may move along the moving unit rail formed on the second column 1412 may be formed on the right of the straight arm moving unit 140. The medical image apparatus 100 may control the straight arm moving unit 140 to vertically slide by using the straight arm driving unit. Accordingly, the straight arm 130 coupled to the straight arm moving unit 140 may vertically move. Because the straight arm moving unit 140 is supported on both sides by the first column 1411 and the second column 1412, the straight arm moving unit 140 may hardly move even when there is vibration due to movement of the arm. Accordingly, the medical image apparatus 100 may obtain a clear medical image.

Figure 15:
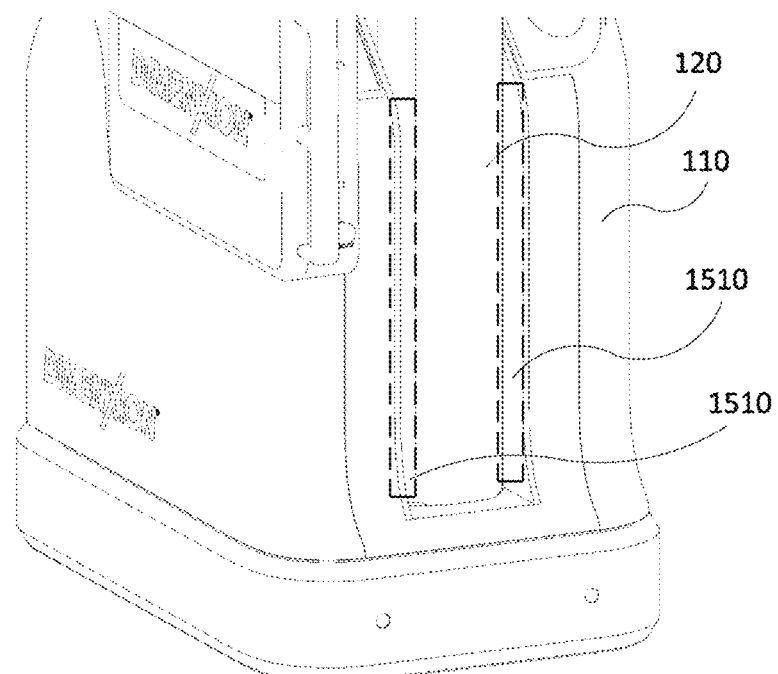
FIG. 15 is a view for describing a medical image apparatus according to an embodiment of the present disclosure.

FIG. 15 is a view for describing a medical image apparatus according to an embodiment of the present disclosure.

The medical image apparatus 100 may include a vibration absorbing portion 1510 formed of an elastic material and vertically extending between the main body 110 and the column 120. The vibration absorbing portion may be formed of a material such as silicone, rubber, or polyurethane. At least some of a left surface, a right surface, and a rear surface of the column 120 may be supported by the main body. That is, at least some of the left surface, the right surface, and the rear surface of the column 120 may contact the main body. As such, because at least a part of a lower portion of the column 120 is supported by the main body 110, even when at least one arm mounted on the column moves, the column 120 coupled to the main body 110 may hardly be shaken. This is because a controller, a battery, a power supply circuit, etc. with a large mass are included in the main body 110 and thus inertia is high. Also, the vibration absorbing portion 1510 may be provided on a surface where the main body 110 and the column 120 contact each other. The vibration absorbing portion 1510 may be formed on the left surface and the right surface of the column 120. Also, the vibration absorbing portion 1510 may also be formed on the rear surface of the column 120. Even when vibration occurs in the column 120, the vibration may be rapidly eliminated. Accordingly, the medical image apparatus 100 may obtain a clear medical image in a fixed state.

The controller 300 may perform various operations for safety based on a signal of the sensor unit 310. Also, the controller 300 may perform various operations for obtaining a clear medical image based on a signal of the sensor unit 310. Various sensors that may be included in the medical image apparatus 100 to ensure safety and obtain a clear medical image will be described.

FIG. 16 is a view for describing a position of a collision avoidance sensor according to an embodiment of the present disclosure.

In FIG. 16, various positions of the collision avoidance sensor will be described. However, the present disclosure is not limited thereto. Also, the collision avoidance sensor may be located at least one of the positions of the collision avoidance sensor of FIG. 16.

Referring to (a) of FIG. 16, the medical image apparatus 100 may include at least one forward collision avoidance sensor 1611, 1612 on a front surface of the main body 110. Although two forward collision avoidance sensors 1611, 1612 are provided in (a) of FIG. 16, the present disclosure is not limited thereto. The forward collision avoidance sensors 1611, 1612 may be located on a bumper portion protruding forward from a lower end of the main body 110.

Referring to (b) of FIG. 16, the medical image apparatus 100 may include at least one forward collision avoidance sensor 1621 on a front surface of the detector 180. Although one forward collision avoidance sensor 1621 is illustrated in (b) of FIG. 16, the present disclosure is not limited thereto. A side collision avoidance sensor 1622 may be formed on a top surface of the detector 180 in (b) of FIG. 16. Referring to (b) of FIG. 16, when the straight arm 130 is parallel to the ground, the side collision avoidance sensor 1622 may face upward. Unlike in (b) of FIG. 16, when the straight arm 130 rotates to be perpendicular to the ground, the side collision avoidance sensor 1622 may face leftward or rightward. When an angle between the straight arm 130 and the ground is equal to or greater than a preset threshold angle or equal to or less than 90°, the medical image apparatus 100 may control the side collision avoidance sensor 1622 to operate. The threshold angle may be equal to and greater than 30° and equal to or less than 90°. However, the present disclosure is not limited thereto, and the side collision avoidance sensor 1622 may always operate. The medical image apparatus 100 may prevent the straight arm 130, the source arm 150, or the detector arm 170 from colliding with a side obstacle of the medical image apparatus 100 by using the side collision avoidance sensor 1622. Accordingly, the safety of the medical image apparatus 100 may be enhanced.

Referring to (c) of FIG. 16, the medical image apparatus 100 may include at least one rear collision avoidance sensor 1631, 1632 on a rear surface of the main body 110. Although two rear collision avoidance sensors 1631, 1632 are provided in (c) of FIG. 16, the present disclosure is not limited thereto. The rear collision avoidance sensors 1631, 1632 may be located on a lower end of the main body 110. The medical image apparatus 100 may prevent the medical image apparatus 100 from colliding with a rear obstacle based on the rear collision avoidance sensors 1631, 1632. For example, the medical image apparatus 100 may move backward under the control of a user. The user may guide a posture of a patient while being positioned in front of the medical image apparatus 100. The user may move the medical image apparatus 100 backward by using a wired/wireless controller when necessary. In this case, when the rear collision avoidance sensors 1631, 1632 detect a solid object, the medical image apparatus 100 may stop despite the user's input. Also, the medical image apparatus 100 may output an alarm in the form of light or sound. As such, the medical image apparatus 100 may safely move based on the rear collision avoidance sensors 1631, 1632.

Referring to (d) of FIG. 16, the medical image apparatus 100 may include at least one side collision avoidance sensor 1641, 1642 on the detector 180. When the straight arm 130 is horizontal, the side collision avoidance sensor 1641 may face the right or the left of the medical image apparatus 100. Also, when the straight arm 130 is vertical, the side collision avoidance sensor 1641 may face the top or the bottom of the medical image apparatus 100. When the straight arm 130 is horizontal, the side collision avoidance sensor 1642 may face the top or the bottom of the medical image apparatus 100. Also, when the straight arm 130 is vertical, the side collision avoidance sensor 1642 may face the left or the right of the medical image apparatus 100. The side collision avoidance sensor 1642 of (d) of FIG. 16 may be a sensor at the same position as the side collision avoidance sensor 1622 of (b) of FIG. 16. When an angle between the straight arm 130 and the ground is equal to or greater than 1° and is equal to or less than a preset second threshold angle, the medical image apparatus 100 may control the side collision avoidance sensor 1642 to operate. When an angle between the straight arm 130 and the ground is equal to or greater than a preset first threshold angle and equal to or less than 90°, the medical image apparatus 100 may control the side collision avoidance sensor 1642 to operate. The first threshold angle is equal to or greater than 30° and equal to or less than 90°. Also, the second threshold angle may be equal to or greater than 0° and equal to or less than 60°. However, the present disclosure is not limited thereto, and the side collision avoidance sensors 1641, 1642 may always operate. The medical image apparatus 100 may prevent the straight arm 130, the source arm 150, or the detector arm 170 from colliding with a side obstacle of the medical image apparatus 100 by using the side collision avoidance sensors 1641, 1642. Accordingly, the safety of the medical image apparatus 100 may be enhanced.

Although not shown in FIG. 16, as shown in FIG. 7, the forward collision avoidance sensor 734 may be provided on a front surface of the source arm 150. The forward collision avoidance sensor and the side collision avoidance sensor may be included in the sensor unit 310 of FIG. 3.

Figure 17:
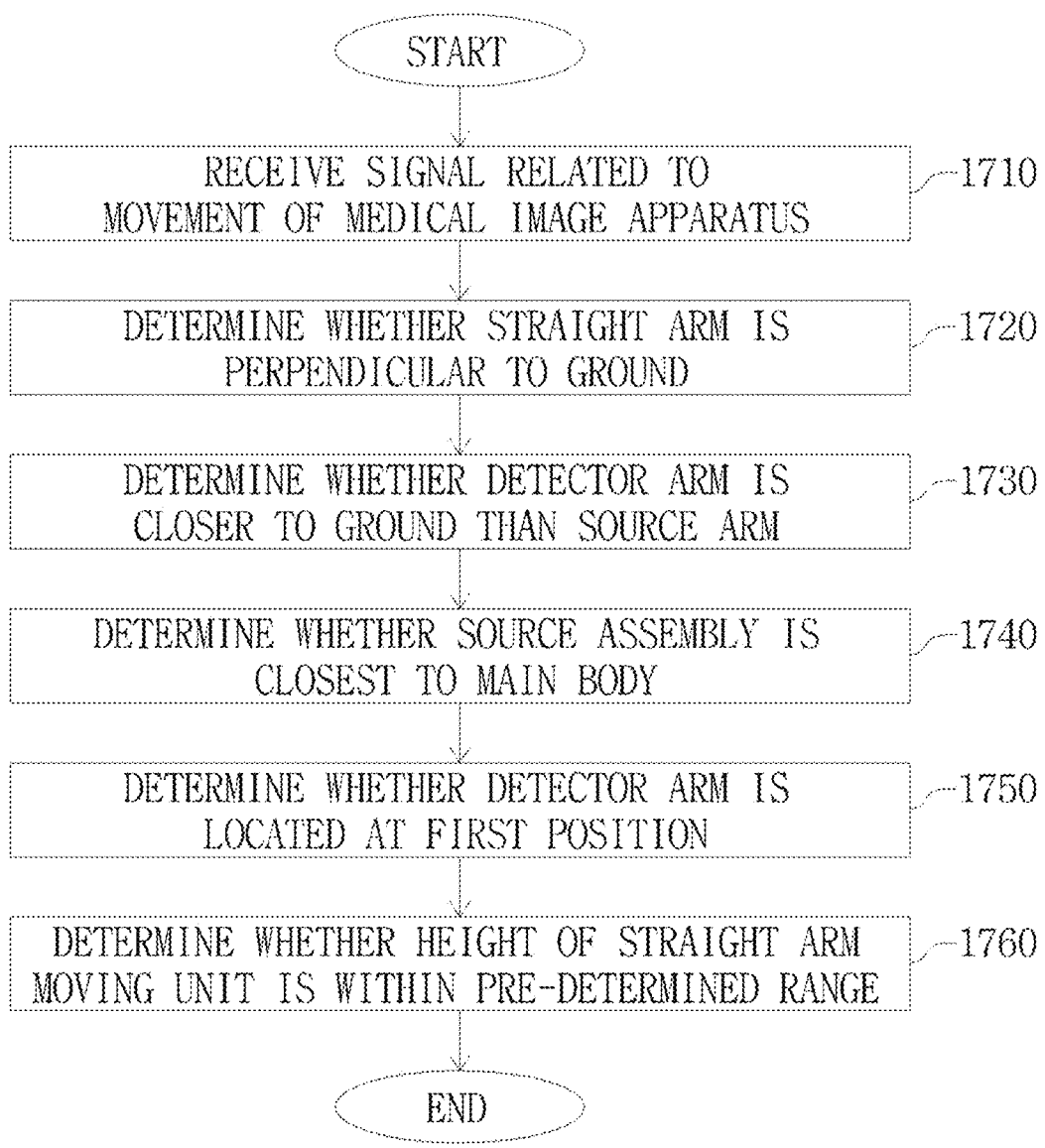
FIG. 17 is a diagram for describing an operation of a medical image apparatus according to an embodiment of the present disclosure.

FIG. 17 is a diagram for describing an operation of a medical image apparatus according to an embodiment of the present disclosure.

The sensor unit 310 of the medical image apparatus 100 may further include a source encoder. The source encoder may be included in the source assembly 160. The source encoder may be an element for measuring a position of the source assembly 160 on the source arm 150. When the source assembly 160 is located at a pre-determined position based on the source encoder, the controller 300 may control the medical image apparatus 100 to be movable. For example, the source assembly 160 is closest to the main body 110 based on the source encoder, the controller 300 may control the medical image apparatus 100 to be movable.

The sensor unit 310 of the medical image apparatus 100 may include a rotation encoder. The rotation encoder may be included in the straight arm 130 or the straight arm moving unit 140. The rotation encoder may be an element for measuring a rotation angle of the straight arm 130 with respect to the column 120. The controller 300 may perform a step of determining whether the straight arm is perpendicular to the ground based on the rotation encoder. When the straight arm 130 is perpendicular to the ground, the controller 300 may control the medical image apparatus 100 to be movable.

As described above, even if a user commands to move the main body 110 through the input unit 350 or releases travel locking of the medical image apparatus, when a pre-determined condition is not satisfied, the medical image apparatus 100 may not travel. In more detail, the medical image apparatus 100 may determine a condition under which the medical image apparatus 100 is movable as follows.

In order to move the medical image apparatus 100 to a position of a patient, the user may operate a wheel of the main body 110. The user may move the medical image apparatus 100 by using a joystick included in the input unit 350. The medical image apparatus 100 may perform a step 1710 of receiving a signal related to movement of the medical image apparatus 100 through the input unit 350. The medical image apparatus 100 may perform a step of determining whether a posture of the medical image apparatus 100 is a posture suitable for travel. The medical image apparatus 100 may further perform the following steps in order to determine whether a posture of the medical image apparatus 100 is a posture suitable for travel.

The medical image apparatus 100 may perform a step 1720 of determining whether the straight arm 130 is perpendicular to the ground. The medical image apparatus 100 may obtain an angle of the straight arm 130 with respect to the ground or an angle of the straight arm 130 with respect to the column 120 based on the rotation encoder. When an angle of the straight arm 130 with respect to the ground is equal to or greater than a pre-determined first threshold angle and equal to or less than 90°, the medical image apparatus 100 may determine that the straight arm 130 is perpendicular to the ground. Although the above has been described based on an angle of the straight arm 130 with respect to the ground, a similar description may be made even with an angle with respect to the column 120 and thus a repeated description will be omitted.

When the straight arm 130 is not vertical, the medical image apparatus 100 may output a signal indicating to make the straight arm 130 vertical through the output unit 340. When the straight arm 130 is horizontal, both ends of the straight arm 130 may protrude out of a left surface and a right surface of the main body 110 and may collide with a person. Accordingly, the medical image apparatus 100 may control the medical image apparatus 100 to travel when the straight arm 130 is perpendicular to the ground.

When the medical image apparatus 100 is vertical to the straight arm 130, the medical image apparatus 100 may control the medical image apparatus 100 to travel based on the input unit 350. Also, the lock release button 732, 1930, 1940 is pressed while the medical image apparatus 100 travels, the straight arm 130 may not rotate. The medical image apparatus 100 may determine whether the medical image apparatus 100 is traveling based on whether the wheel rotates.

When the straight arm 130 is vertical, the medical image apparatus 100 may determine a step 1730 of determining whether the detector arm 170 is closer to the ground than the source arm 150. The medical image apparatus 100 may determine whether the detector arm 170 is closer to the ground than the source arm 150 based on the rotation encoder. The rotation encoder may obtain an angle of 360° of the straight arm 130 with respect to the ground. For example, when the straight arm 130 is perpendicular to the ground and the detector arm 170 is located lower than the source arm 150, the rotation encoder may output 0°. Also, when the straight arm 130 is parallel to the ground and the detector arm 170 is located on the right of the medical image apparatus 100, the rotation encoder may output 90°. Also, when the straight arm 130 is perpendicular to the ground and the source arm 150 is located lower than the detector arm 170, the rotation encoder may output 180°. Also, when the straight arm 130 is parallel to the ground and the detector arm 170 is located on the left of the medical image apparatus 100, the rotation encoder may output 270°. When the straight arm 130 is perpendicular to the ground and the detector arm 170 is located lower than the source arm 150, the rotation encoder may output 360°. Of course, 360° may be equal to 0°.

When an angle output from the rotation encoder is equal to or greater than a third threshold angle and equal to or less than a fourth threshold angle, the medical image apparatus 100 may determine that the detector arm 170 is closer to the ground than the source arm 150. The third threshold angle may be equal to or greater than −30° and equal to or less than 0°. The fourth threshold angle may be equal to or greater than 0° and equal to or less than 30°. Because the step 1730 overlaps the step 1720, the step 1720 may be omitted. However, the present disclosure is not limited thereto.

The step 1730 may be performed by using a side collision avoidance sensor included in the detector 180. The detector

180 may include the side collision avoidance sensor 1641 of FIG. 16. When the detector 180 is close to the ground, the side collision avoidance sensor 1641 may recognize the ground. When the side collision avoidance sensor 1641 recognizes the ground, the medical image apparatus 100 may determine that the detector arm 170 is closer to the ground than the source arm 150.

Also, the step 1730 may be performed by using an acceleration sensor or a gyro sensor. The medical image apparatus 100 may determine a direction of gravity by using the acceleration sensor or the gyro sensor included in the detector 180. When a direction from the detector 180 toward the source assembly 160 is different from the direction of the gravity, the medical image apparatus 100 may determine that the detector arm 170 is closer to the ground than the source arm 150.

When the detector arm 170 is not closer to the ground than the source arm 150, the medical image apparatus 100 may output a signal indicating to make the straight arm 130 vertical through the output unit 340. Because the source assembly 160 is a sensitive device and includes an assembly of various elements, a clear medical image may be obtained only when the source assembly 160 is not subjected to impact. When the source assembly 160 is close to the ground, the source assembly 160 is likely to collide with the ground or a protruding object on the ground. Accordingly, the medical image apparatus 100 may travel when the source assembly 160 is located higher than the detector 180.

When the detector arm 170 is closer to the ground than the source arm 150, the medical image apparatus 100 may drive the wheel based on an input of the input unit 350. However, the present disclosure is not limited thereto. When the detector arm 170 is closer to the ground than the source arm 150, the medical image apparatus 100 may perform a step 1740 of determining whether the source assembly 160 is closest to the main body 110. The medical image apparatus 100 may determine whether the source assembly 160 is closest to the main body 110 based on the source encoder. When the source assembly 160 is within a pre-determined distance from the main body 110 or the straight arm 130, the medical image apparatus 100 may determine that the source assembly 160 is closest to the main body 110. When a measurement value of the source encoder is within a pre-determined range, the medical image apparatus 100 may determine that the source assembly 160 is closest to the main body 110.

When the source assembly 160 is not closest to the main body 110, the medical image apparatus 100 may control the source assembly 160 to be automatically close to the main body 110. Also, when the source assembly is not closest to the main body 110, the medical image apparatus 100 may output a signal indicating to move the source assembly 160 closer to the main body 110 through the output unit 340. When the source assembly 160 is far from the main body 110, the center of weight of the medical image apparatus 100 may be relatively at the front. Accordingly, the medical image apparatus 100 is likely to fall forward due to impact while traveling. Accordingly, the medical image apparatus 100 may allow the source assembly 160 to be close to the main body 110 while traveling.

When the source assembly 160 is closest to the main body 110, the medical image apparatus 100 may drive the wheel based on an input of the input unit 350.

The medical image apparatus 100 may perform a step 1750 of determining whether the detector arm 170 is located at a first position. As described above, the first position may indicate a position of the detector arm 170 when a distance between the detector 180 and the source assembly 160 is a first distance. The first distance may be, for example, equal to or greater than 90 mm and equal to or less than 110 mm. Although the step 1750 is performed after the step 1740 in FIG. 17, the present disclosure is not limited thereto. The step 1750 may be performed before or after the step 1720, the step 1730, the step 1740, or the step 1760.

The medical image apparatus 100 may determine whether the detector arm 170 is located at the first position based on a detector encoder included in a detector driving unit. When a measurement value of the detector encoder is within a pre-determined range, the medical image apparatus 100 may determine that the detector arm 170 is located at the first position.

When the detector arm 170 is not located at the first position, the medical image apparatus 100 may control the detector arm 170 to automatically move to the first position. However, the present disclosure is not limited thereto, and the medical image apparatus 100 may output a signal indicating to move the detector arm 170 to the first position through the output unit 340. In order to firmly couple the straight arm 130 to the detector arm 170, the detector arm 170 may have to be at the first position. Accordingly, because the medical image apparatus 100 travels when the detector arm 170 is at the first position, the durability of the medical image apparatus 100 may be increased.

When the detector arm 170 is at the first position, the medical image apparatus 100 may drive the wheel based on an input of the input unit 350.

The medical image apparatus 100 may perform a step 1760 of determining whether a height of the straight arm moving unit 140 on the column 120 is within a pre-determined range. Although the step 1760 is performed after the step 1750 in FIG. 17, the present disclosure is not limited thereto. The step 1760 may be performed before or after the step 1710, the step 1720, the step 1730, the step 1740, or the step 1750. A height of the straight arm moving unit 140 may be determined by an encoder of a straight arm driving unit. The encoder of the straight arm driving unit may be a sensor for measuring a height of the straight arm 130 or the straight arm moving unit 140 on the column 120. When a height of the straight arm moving unit 140 is within a pre-determined range, the detector arm 170 may be separated by a certain distance from the ground. The certain distance may be equal to or greater than 3 cm and equal to or less than 50 cm.

When the height of the straight arm moving unit 140 is not within the pre-determined range, the medical image apparatus 100 may control the height of the straight arm moving unit 140 to be automatically within the pre-determined range. However, the present disclosure is not limited thereto, and the medical image apparatus 100 may output a signal indicating to move the height of the straight arm moving unit 140 to be within the pre-determined range through the output unit 340. When the height of the straight arm moving unit 140 is within the pre-determined range, the detector may be prevented from colliding with a protrusion on the ground. Accordingly, the durability of the medical image apparatus 100 may be increased.

As such, because a posture of the medical image apparatus 100 is checked before the medical image apparatus 100 travels, the medical image apparatus 100 may safely travel. In more detail, people around the medical image apparatus 100 may be protected, and the medical image apparatus 100 may be prevented from being subjected to impact. Accordingly, the safety of the medical image apparatus 100 may be ensured and the durability of the medical image apparatus 100 may be increased.

Additionally, the medical image apparatus 100 may perform a step of determining whether a parking brake is locked. When the parking brake is locked, the medical image apparatus 100 may perform a step of outputting a signal indicating that the parking brake is locked through the output unit 340. When the parking brake is not locked, the medical image apparatus 100 may control the medical image apparatus 100 to move based on a signal of the input unit 350.

Figure 18:
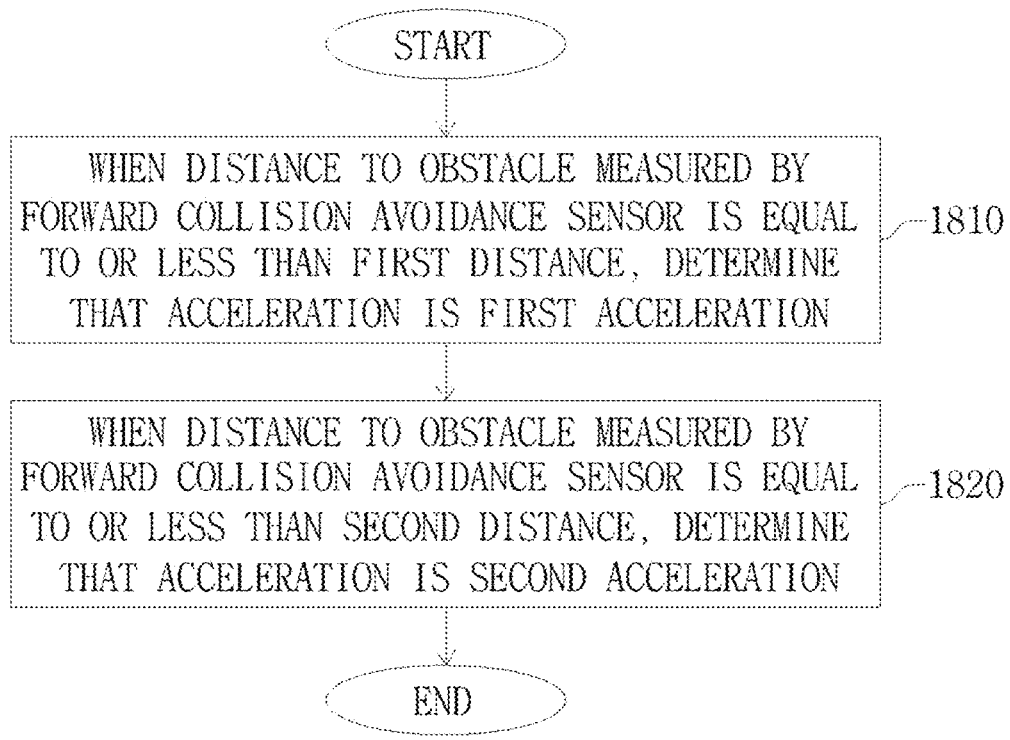
FIG. 18 is a flowchart for describing an operation of a medical image apparatus according to an embodiment of the present disclosure.

FIG. 18 is a flowchart for describing an operation of a medical image apparatus according to an embodiment of the present disclosure.

When a distance to an obstacle measured by a forward collision avoidance sensor is equal to or less than a third distance, the controller 300 may perform a step 1810 of determining that an acceleration is a first acceleration. The forward collision avoidance sensor may be at least one of sensors described in FIGS. 7 and 16. The acceleration in the step 1810 may refer to a deceleration for decelerating the medical image apparatus 100. That is, the first acceleration may be negative with respect to a direction in which the medical image apparatus 100 travels.

When a distance to an obstacle measured by the forward collision avoidance sensor is equal to or less than a fourth distance, the controller 300 may perform a step 1820 of determining that an acceleration is a second acceleration. An acceleration in the step 1820 may refer to a deceleration for reducing a speed of the medical image apparatus 100. That is, the second acceleration may be negative with respect to a direction in which the medical image apparatus 100 travels. The third distance may be greater than the fourth distance. Also, an absolute value of the first acceleration may be less than an absolute value of the second acceleration.

When controlled as above, the medical image apparatus 100 may be decelerated at the first acceleration when there is a sufficient distance to an obstacle, and may be decelerated at the second acceleration when an obstacle is too close. In the step 1810 and the step 1820, the medical image apparatus 100 may slowly change an absolute value of an acceleration from 0 to an absolute value of the first acceleration, or may slowly change from the absolute value of the first acceleration to an absolute value of the second acceleration. When the medical image apparatus 100 rapidly accelerates, the medical image apparatus 100 may fall forward due to inertia. Accordingly, except an unavoidable case such as an obstacle that is too close, the medical image apparatus 100 may control an acceleration not to be high, thereby ensuring the safety of the medical image apparatus 100.

As described above, the detector 180 may be located lower than the source arm 150 while the medical image apparatus 100 travels. Also, as described with reference to FIG. 16, the forward collision avoidance sensor 1621 may be provided at the front of the detector 180. When the medical image apparatus 100 travels, the forward collision avoidance sensor 1621 may generate information about whether there is an obstacle (hill) ahead. The medical image apparatus 100 may decelerate the medical image apparatus 100 as described above, and may move the straight arm moving unit 140 upward by a certain distance. That is, when the medical image apparatus 100 receives a signal indicating that there is an obstacle ahead from the forward collision avoidance sensor 1621, the medical image apparatus 100 may move upward the straight arm moving unit 140 by a certain distance. When the straight arm moving unit 140 moves upward by a certain distance, the detector 180 may also move upward by a certain distance. Accordingly, the medical image apparatus 100 may prevent the front of the detector 180 from colliding with an obstacle (hill). When there is a high obstacle, a user may recognize the high obstacle. However, when there is a low obstacle, it may be difficult for the user to recognize the obstacle. The medical image apparatus 100 may automatically recognize an obstacle ahead to prevent the detector from colliding with the obstacle. Also, when there is no obstacle, the medical image apparatus 100 may move downward the straight arm moving unit 140 by a certain distance.

Figure 19:
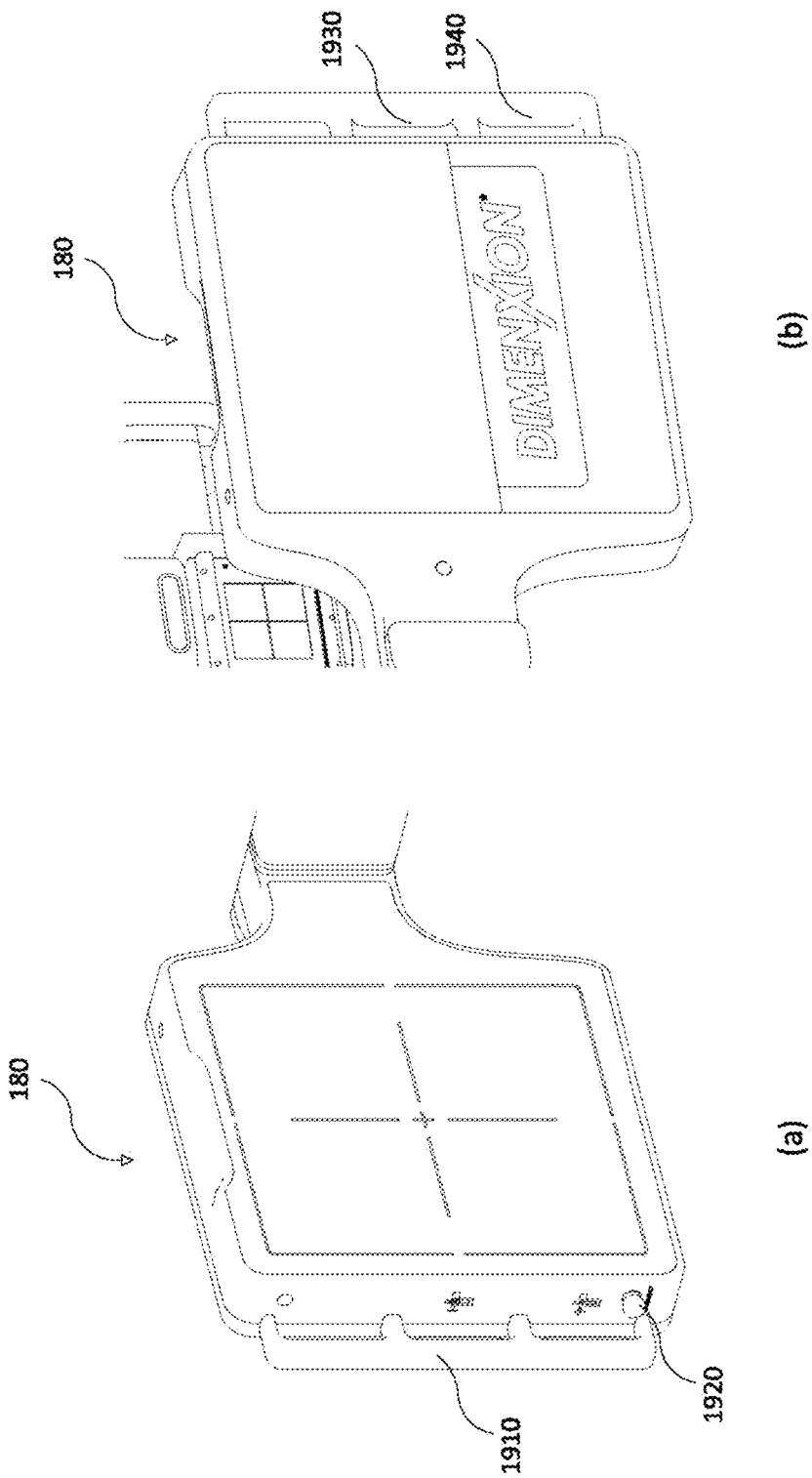
FIG. 19 is a view for describing a detector according to an embodiment of the present disclosure.

FIG. 19 is a view for describing the detector 180 according to an embodiment of the present disclosure.

A sensor included in the detector 180 has been described in FIG. 16, and thus a description thereof will be omitted in FIG. 19. (a) of FIG. 19 is a view illustrating the detector 180 viewed from a viewpoint. (b) of FIG. 19 is a view illustrating the detector 180 viewed from another viewpoint.

Referring to (a) of FIG. 19, a handle 1910 may be formed at a front end of the detector 180. As shown in FIG. 19, the handle 1910 may be coupled to the detector 180 at four portions, and the handle 1910 and the detector 180 may be firmly coupled to each other. Because the handle 1910 is formed at the front end of the detector 180, a user may rotate the straight arm 130 at a position not colliding with the source arm 150 or the detector arm 170. Accordingly, the safety of the medical image apparatus 100 may be improved. Also, because a patient may maintain his/her posture while holding the handle 1910, the medical image apparatus 100 may obtain a clear medical image.

Referring to (b) of FIG. 19, the lock release buttons 1930, 1940 may be located behind the handle 1910. The lock release buttons 1930, 1940 may be buttons for determining whether to rotate the straight arm 130 with respect to the column 120. When the user is to rotate the straight arm 130, the user may press the lock release buttons 1930, 1940 and may rotate the straight arm 130. When the lock release buttons 1930, 1940 are pressed, the straight arm 130 may rotate. However, the present disclosure is not limited thereto, and the straight arm 130 may rotate when an additional condition is further satisfied.

The detector 180 may include two lock release buttons 1930, 1940. The detector 180 may be close to a patient and the patient may accidentally press a lock release button. The medical image apparatus 100 may control the straight arm 130 to rotate only when both the two lock release buttons 1930, 1940 are pressed. Accordingly, even when a patient accidentally presses one lock release button, the straight arm 130 may not rotate.

Referring to (a) of FIG. 19, the detector 180 may include an emergency button 1920. In a situation where an accident may occur, the emergency button 1920 may be pressed by the user. When the emergency button 1920 is pressed, the medical image apparatus 100 may stop a wheel of the main body 110. When the medical image apparatus 100 is likely to collide with a person or a wall, the user may press the emergency button 1920 and the medical image apparatus 100 may rapidly brake the wheel of the main body 110, thereby preventing damage due to collision. Also, even if the user does not intentionally press the emergency button 1920, when the medical image apparatus 100 moves forward and collides with an obstacle, the emergency button 733 that is located at a foremost position may be pressed and additional damage to the obstacle or the medical image apparatus 100 may not occur. Also, when the emergency button 1920 is pressed, the medical image apparatus 100 may stop at least one of movement of the source assembly 160, movement of the detector arm 170, vertical movement of the straight arm 130, or rotation of the straight arm 130, to prevent an emergency.

The medical image apparatus 100 may perform the following process, when the user is to make the straight arm 130 vertical in a state where the straight arm 130 is horizontal. In more detail, when a lock release button is pressed, the medical image apparatus 100 may determine that the user is to rotate the straight arm 130.

The medical image apparatus 100 may perform a step of determining a posture of the straight arm 130. For example, the medical image apparatus 100 may perform a step of determining whether the straight arm 130 is horizontal based on a rotation encoder.

When the straight arm 130 is horizontal, the medical image apparatus 100 may perform a step of obtaining a height of the straight arm moving unit 140 on the column 120 based on an encoder of a straight arm driving unit. Also, the medical image apparatus 100 may perform a step of determining whether the height of the straight arm moving unit 140 is within a pre-determined threshold height range. When the height of the straight arm moving unit 140 is not within the pre-determined threshold height range, the medical image apparatus 100 may not rotate the straight arm 130. When the height of the straight arm moving unit 140 is not within the pre-determined threshold height range, the medical image apparatus 100 may mot rotate the straight arm 130 even when the user presses the lock release button 731, 1930, 1940. The medical image apparatus 100 may output a signal indicating to adjust the height of the straight arm moving unit 140 through the output unit 340.

When the user presses the lock release button 732, 1930, 1940 and the height of the straight arm moving unit 140 is within the pre-determined threshold height range, the medical image apparatus 100 may control the straight arm 130 to rotate. When the height of the straight arm moving unit 140 is within the pre-determined threshold height range, the medical image apparatus 100 may control the straight arm 130 to rotate, thereby preventing the detector 180 or the source arm 150 from contacting the ceiling or the ground during rotation.

However, the present disclosure is not limited thereto, and the medical image apparatus 100 may store an allowable rotation angle determination table in which an allowable angle range of the straight arm 130 and the ground according to the height of the straight arm moving unit 140 is stored. Alternatively, the medical image apparatus 100 may store an allowable rotation angle determination formula for deriving an allowable angle range of the straight arm 130 and the ground based on the height of the straight arm moving unit 140. When the user presses the lock release button 732, 1930, 1940, the medical image apparatus 100 may control the straight arm 130 to rotate. Also, the medical image apparatus 100 may obtain an allowable angle range by applying the height of the straight arm moving unit 140 to the allowable rotation angle determination table or the allowable rotation angle determination formula. The medical image apparatus 100 may control an angle of the straight arm 130 to be within the allowable angle range. That is, when the user attempts to rotate the straight arm 130 out of the allowable angle range, the medical image apparatus 100 may operate the brake.

As described with reference to FIGS. 7 and 16, at least one of the detector 180 or the main body 110 may include a side collision avoidance sensor. The side collision avoidance sensor may recognize whether a solid object is located on the left, right, upper, or lower side of the medical image apparatus 100 or is located between the detector 180 and the source assembly 160. When the medical image apparatus 100 receives a signal indicating that there is a solid object located on the left, right, upper, or lower side, or between the detector 180 and the source assembly 160 from the side collision avoidance sensor regardless of a rotation angle of the straight arm 130, the medical image apparatus 100 may prevent rotation of the straight arm 130.

The medical image apparatus 100 may perform a step of determining whether the straight arm 130 is perpendicular to the ground and the side collision avoidance sensor recognizes a solid object. When the straight arm 130 is perpendicular to the ground and the side collision avoidance sensor recognizes a solid object, the medical image apparatus 100 may control the straight arm 130 not to be rotatable. When the straight arm 130 is perpendicular to the ground and the side collision avoidance sensor recognizes a solid object, even if the user presses the lock release button 732, 1930, 1940, the medical image apparatus 100 may not rotate the straight arm 130. The medical image apparatus 100 may output a signal indicating that there is a side obstacle of the medical image apparatus 100 through the output unit 340. The medical image apparatus 100 may first determine whether there is a slid object on the left, right, upper, or lower side of the medical image apparatus 100 or between the detector 180 and the source assembly 160 during rotation of the straight arm 130, to ensure that the straight arm 130 safely rotates.

As described with reference to FIGS. 7, 16, and 19, the source arm 150 and the detector arm 170 may include the sensor unit 310 or the input unit 350 at the front. The sensor unit 310 may be, for example, a collision avoidance sensor. Also, the input unit 350 may be a lock release button or an emergency button.

Figure 21:
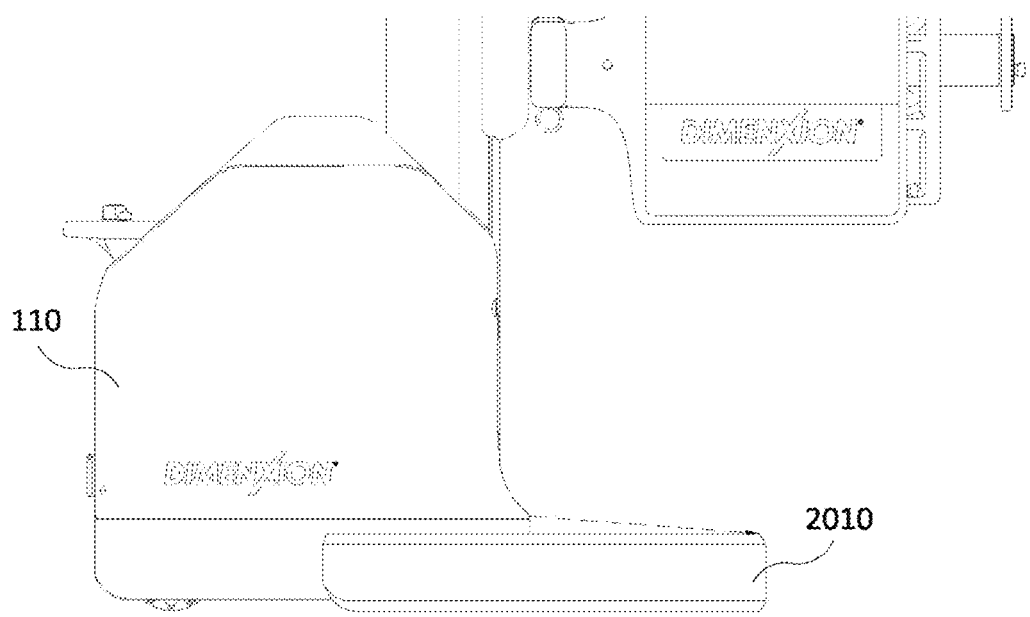
FIG. 21 is a view illustrating a main body according to an embodiment of the present disclosure.

FIG. 20 is a view illustrating a main body according to an embodiment of the present disclosure. Also, FIG. 21 is a view illustrating a maim body according to an embodiment of the present disclosure. Also, FIG. 22 is a view illustrating a main body according to an embodiment of the present disclosure.

Figure 22:
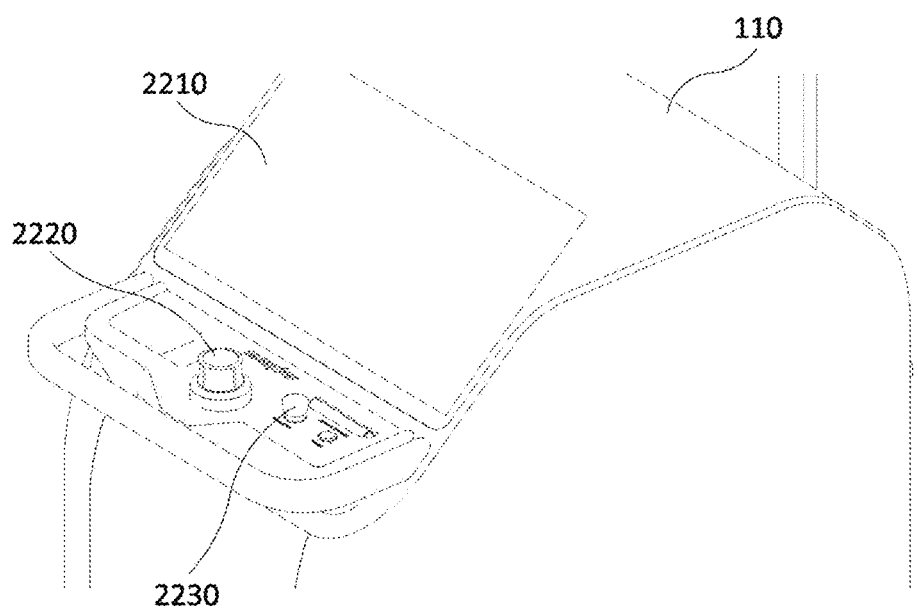
FIG. 22 is a view illustrating a main body according to an embodiment of the present disclosure.

FIGS. 20 through 22 are views illustrating the medical image apparatus 100 viewed at different angles.

Referring to (a) of FIG. 20, the main body 110 may include a wheel cover 2010 for covering a wheel on both sides. The wheel cover 2010 may protrude from left and right surfaces of the main body 110. Accordingly, when the main body 110 collides a solid object on a side, the wheel cover 2010 may first contact the solid object. The wheel cover 2010 may extend in a front-back direction and may cover both a front wheel and a rear wheel. The wheel cover 2010 may prevent a foreign material from contacting the wheel. That is, the wheel cover 2010 may prevent a foreign material from being caught on the wheel. Accordingly, the safety of the medical image apparatus 100 may be increased.

Referring to (b) of FIG. 20, a travel display portion may be provided outside the wheel cover 2010. The travel display portion may display information related to travel of the medical image apparatus 100. The information related to travel may be information indicating a travel direction, a travel speed, or the existence of travel.

For example, when the medical image apparatus 100 travels forward, the travel display portion may output an icon or text indicating forward movement. The icon may be a figure such as a curve, a straight line, a circle, an oval, a square, or an arrow, or a character. Also, the travel display portion may display the information related to travel indicating a direction in which the medical image apparatus 100 is to move. For example, when a user commands to move forward, before movement, the travel display portion may display information indicating that the medical image apparatus 100 is to move forward by using a movement direction of an icon or text. Also, the travel display portion may be turned off while the medical image apparatus 100 is stopped. However, when the user starts traveling, the travel display portion may be turned on to notify people around that the medical image apparatus is preparing to travel.

When the wheel cover 2010 covers the wheel, people around the medical image apparatus may not know whether the medical image apparatus 100 is traveling or is preparing to travel, or a travel direction. In particular, because a Mecanum wheel used in the medical image apparatus 100 may move not only in the front-back direction but also in a left-right direction, people around of the medical image apparatus may not able to prepare for sudden movement of the medical image apparatus 100. Because the wheel cover 2010 of the medical image apparatus 100 of the present disclosure includes the travel display portion and notifies a movement direction and whether the medical image apparatus is preparing to move, people around of the medical image apparatus 100 may predict the movement direction of the medical image apparatus 100, and may know whether the medical image apparatus 100 is traveling or is preparing to travel.

When the medical image apparatus 100 is in an imaging mode, the controller 300 may perform a step of moving downward the wheel cover 2010 to contact the ground. The imaging mode may refer to a step at which the medical image apparatus 100 prepares to capture a medical image or a step at which the medical image apparatus 100 captures a medical image. The medical image apparatus 100 may determine a mode of the medical image apparatus 100 according to an input of the user or automatically. Also, when the medical image apparatus 100 is stopped and a signal related to preparation for medical imaging is input, the medical image apparatus 100 may be in an imaging mode. When the source 810 is turned on, information about a patient who is to be imaged is input, or the medical image apparatus 100 recognizes a beacon of an imaging site, the medical image apparatus 100 may determine that a mode is an imaging mode. The beacon may be a device for broadcasting a signal having a specific pattern. The medical image apparatus 100 may receive the signal having the specific pattern and may determine a position of the medical image apparatus 100. Also, the medical image apparatus 100 may receive the signal having the specific pattern and may determine that the medical image apparatus 100 is preparing for imaging. When a hospital room and a patient are matched and are stored in a server or the medical image apparatus, the medical image apparatus 100 may automatically derive a patient scheduled to be imaged based on the signal having the specific pattern.

The main body 110 may include a wheel cover driving unit for moving the wheel cover 2010. A bottom surface of the wheel cover 2010 may be finished with an elastic material. For example, the bottom surface of the wheel cover 2010 may be formed of a material such as rubber, silicone, or polyurethane. The wheel cover 2010 may contact the ground with high friction to prevent movement of the medical image apparatus 100. The wheel cover 2010 may be a weight. That is, the wheel cover 2010 may have a certain weight or more. Alternatively, the wheel cover 2010 may be a replaceable battery. When the wheel cover 2010 moves downward, the center of weight may be lowered. Accordingly, the safety of the medical image apparatus 100 may be increased.

When the medical image apparatus 100 is in an imaging mode, the medical image apparatus 100 may move downward the wheel cover 2010 by using the wheel cover driving unit so that the wheel cover 2010 contacts the ground. Accordingly, the wheel cover 2010 may function as a support of the main body 110. The wheel cover 2010 may contact the ground and may reduce vibration occurring in the medical image apparatus 100.

When the medical image apparatus is in a travel mode, the controller 300 may perform a step of moving upward the wheel cover. When the user is to move the medical image apparatus 100 through the input unit 350, the medical image apparatus may be in a travel mode. The medical image apparatus 100 may move upward the wheel cover 2010, to be in a travelable state.

Referring to FIG. 21, when the medical image apparatus 100 is an imaging mode, the controller 300 may further move forward the wheel cover 2010 before moving downward the wheel cover 2010, by using a wheel cover driving unit. As shown in FIG. 21, heavy objects such as the detector 180 and the source assembly 160 may be located in a front portion of the medical image apparatus 100 as shown in FIG. 21. When the wheel cover 2010 moves forward and moves downward, impact may be applied to the detector 180 or the source assembly 160, thereby preventing the medical image apparatus 100 from falling forward. When the medical image apparatus 100 changes to a travel mode, the medical image apparatus 100 may move upward the wheel cover 2010 and then move the wheel cover 2010 backward. The medical image apparatus 100 may be in a travelable state.

Referring back to FIG. 20, the main body 110 may include a camera 2020 for capturing a front image of the main body 110. Referring to FIG. 22, the main body 110 may include a main display portion 2210 for displaying a medical image. The main display portion 2210 may be included in the output unit 340. The main display portion 2210 may display a medical image. Also, the main display portion 2210 may display an image of the camera 2020. The main display portion 2210 may be included in the input unit 350. The main display portion 2210 may be a touchscreen. The main display portion 2210 may receive information related to settings of the medical image apparatus 100, patient information, setting information related to imaging, or an imaging command from a user.

The main body 110 may include a joystick 2220 around the main display portion 2210. The user may move the medical image apparatus 100 by using the joystick 2220 included in the input unit 350. The user may safely control the medical image apparatus 100 while viewing an image of the camera 2020 displayed on the main display portion 2210.

The main body 110 may include an emergency button 2230 around the main display portion 2210. The user may prevent a dangerous situation by pressing the emergency button 2230 in an urgent situation while viewing an image captured by the camera 2020.

When the medical image apparatus 100 is an imaging mode, the controller 300 may perform a step of controlling the main display portion 2210 to display an image related to a medical image. Also, the image related to the medical image may include at least one of a medical image, patient information, a previous medical image of a patient, or medical imaging setting information. When the medical image apparatus 100 is in an imaging mode, the medical image apparatus 100 may display an image related to a medical image, thereby preventing confusion to the user by displaying unnecessary information displayed on the main display portion 2210.

When the medical image apparatus 100 is in a travel mode, the controller 300 may perform a step of controlling the main display portion 2210 to display an image of the camera 2020. Various people may view the medical image apparatus 100 while the medical image apparatus 100 is traveling, and information related to a medical image may be confidential information. Accordingly, because the medical image apparatus 100 displays an image of the camera 2020 and does not display information related to a medical image while traveling, security may be maintained and a front image required for travel may be checked.

Also, when the medical image apparatus 100 is even in an imaging mode, the medical image apparatus 100 may display an image of the camera 2020 on the main display portion 2210 according to an input of the user. The user may have to check an imaging posture of a patient. The user may be a medical staff member specialized in medical imaging, and it may be inconvenient to move toward the patient in order to check a posture of the patient. Also, due to the column 120 or the straight arm 130, it may be difficult for the user to check a posture of the patient. Accordingly, the user may instruct the patient to take a specific posture while checking the patient in front of the medical image apparatus 100 through the camera 2020.

In order to use the medical image apparatus 100, the user may have to perform an authentication procedure. This is because information requiring security may be stored in the medical image apparatus 100, and because the medical image apparatus 100 is movable, there is a risk of theft. When the user turns on the medical image apparatus 100, a lock screen may be displayed on the medical image apparatus 100. After turning on the medical image apparatus 100, the user may bring his/her identification tag to the front of the camera 2020 according to a guide. A barcode quick response (QR) code may be on the identification tag. Alternatively, the user may stand in front of the camera 2020 according to a guide. The medical image apparatus 100 may obtain identification information of the user based on the user's face or an image of the identification tag. Also, when the identification information of the user is valid, the medical image apparatus 100 may unlock a lock screen so that the user manipulates the medical image apparatus 100.

The present disclosure has been particularly shown and described with reference to various embodiments thereof. It will be understood by one of ordinary skill in the art that various changes in form and details may be made therein without departing from the spirit and scope of the present disclosure as defined by the appended claims. The disclosed embodiments should be considered in descriptive sense only and not for purposes of limitation. The scope of the present disclosure is defined only by the following claims, and all the equivalents of the embodiments may also be construed to be in the scope of the present disclosure.

Accordingly, the aforementioned embodiments of the present disclosure may be written into a program that may be executed by a computer, and may be implemented in a universal digital computer for carrying out the program using a computer-readable recording medium. The computer-readable recording medium includes a storage medium, such as a magnetic storage medium (e.g., a ROM, a floppy disk, or a hard disk) or an optical medium (e.g., a compact disc (CD)-ROM or a digital versatile disc (DVD)).

What is claimed is:

1. A medical image apparatus comprising:
    a column vertically coupled to a main body;
    a straight arm moving unit sliding in a longitudinal direction of the column;
    a straight arm coupled to the straight arm moving unit and rotating with respect to the column; and
    a source arm located on a side of the straight arm, perpendicular to the straight arm, and comprising a source driving rail through which a source assembly slides,
    wherein the straight arm is coupled to a moving unit rotating shaft formed on the straight arm moving unit, and is rotatable with respect to the column about the moving unit rotating shaft; and
    the source arm is fixed to the side of the straight arm,
    wherein the source arm passes through a hole formed in the source assembly, and a roller formed in the hole of the source assembly contacts the source driving rail so that the source assembly slides through the source driving rail.

2. The medical image apparatus of claim 1, further comprising a detector arm located on the other side of the straight arm, and comprising a detector driving unit sliding in a longitudinal direction of the straight arm and comprising a detector provided to face the source assembly, the detector arm comprising:
    a detector sliding portion parallel to the straight arm; and
    a detector coupling portion perpendicular to the straight arm and coupled to the detector.

3. The medical image apparatus of claim 2, wherein, due to the detector driving unit, the detector arm is located at a first position where a distance between the detector and the source assembly is a first distance, or is located at a second position where a distance between the detector and the source assembly is a second distance; and
    the first distance is less than the second distance.

4. The medical image apparatus of claim 3, wherein, when the medical image apparatus travels, the straight arm is perpendicular to the ground, and the detector arm is located at the first position and is located closer to the ground than the source arm.

5. The medical image apparatus of claim 2, wherein the detector sliding portion of the detector arm is inserted into a guide hole formed in the straight arm, and slides in the longitudinal direction of the straight arm.

6. The medical image apparatus of claim 2, wherein the straight arm comprises a hole formed in the longitudinal direction in the straight arm and a straight arm balance weight located in the hole, and the straight arm balance weight moves in a direction opposite to a sliding direction of the detector arm.

7. The medical image apparatus of claim 1, wherein a plurality of rollers formed on both sides of the straight arm moving unit are vertically movable along a moving unit rail formed in the column.

8. A medical image apparatus comprising:
    a column vertically coupled to a main body;
    a straight arm moving unit sliding in a longitudinal direction of the column;
    a straight arm coupled to the straight arm moving unit and rotating with respect to the column;
    a source arm located on a side of the straight arm, perpendicular to the straight arm, and comprising a source driving rail through which a source assembly slides;
    a detector arm located on the other side of the straight arm, and comprising a detector driving unit sliding in a longitudinal direction of the straight arm and comprising a detector provided to face the source assembly, the detector arm comprising:
a detector sliding portion parallel to the straight arm; and
a detector coupling portion perpendicular to the straight arm and coupled to the detector,
wherein the straight arm is coupled to a moving unit rotating shaft formed on the straight arm moving unit, and is rotatable with respect to the column about the moving unit rotating shaft; and
the source arm is fixed to the side of the straight arm,
wherein the detector sliding portion of the detector arm is inserted into a guide hole formed in the straight arm, and slides in the longitudinal direction of the straight arm.

* * * * *